(12) United States Patent
Huang

(10) Patent No.: US 9,382,584 B2
(45) Date of Patent: Jul. 5, 2016

(54) METHODS AND SYSTEMS FOR DIRECT SEQUENCING OF SINGLE DNA MOLECULES

(71) Applicant: The Regents of the University of California, Oakland, CA (US)

(72) Inventor: Xiaohua Huang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 11 days.

(21) Appl. No.: 14/229,621

(22) Filed: Mar. 28, 2014

(65) Prior Publication Data

US 2014/0295412 A1    Oct. 2, 2014

Related U.S. Application Data

(63) Continuation of application No. 13/133,987, filed as application No. PCT/US2009/067697 on Dec. 11, 2009, now abandoned.

(60) Provisional application No. 61/121,809, filed on Dec. 11, 2008.

(51) Int. Cl.
*C12N 9/12* (2006.01)
*C12Q 1/68* (2006.01)

(52) U.S. Cl.
CPC ............ *C12Q 1/6869* (2013.01); *C12N 9/1252* (2013.01)

(58) Field of Classification Search
None
See application file for complete search history.

(56) References Cited

U.S. PATENT DOCUMENTS

| | | | | |
|---|---|---|---|---|
| 5,576,204 A | * | 11/1996 | Blanco | C12N 9/1252 435/193 |
| 6,908,736 B1 | * | 6/2005 | Densham | C07H 21/00 435/174 |
| 6,982,146 B1 | | 1/2006 | Schneider et al. | |
| 8,999,676 B2 | * | 4/2015 | Emig | C12N 9/1252 435/194 |
| 2003/0059778 A1 | | 3/2003 | Berlin et al. | |
| 2006/0078937 A1 | | 4/2006 | Korlach et al. | |

OTHER PUBLICATIONS

Berman et al., EMBO Journal vol. 26, pp. 3194-3505, Jan. 2007.*
The International Search Report and Written Opinion from PCT/US2009/067697, dated Aug. 25, 2010.
http:/ww.lifetechnologies.com/us/en/home/references/molecular-probes-the-handbood/technical-notes-and-product-highlights/fluorescence-resonance-energy-transfer-fret.html; accessed Mar. 3, 2014.

* cited by examiner

*Primary Examiner* — Richard Hutson
(74) *Attorney, Agent, or Firm* — Kilpatrick Townsend & Stockton LLP

(57) ABSTRACT

The invention provides improved methods for sequencing nucleic acids, e.g., for medical applications and biomedical research. The disclosed methods can be applied to rapid personalized medicine, genetic diagnosis, pathogen identification, and sequencing species genomes.

13 Claims, 13 Drawing Sheets

METHODS AND SYSTEMS FOR DIRECT SEQUENCING OF SINGLE DNA MOLECULES

CROSS-REFERENCES TO RELATED APPLICATIONS

The present application is a continuation of U.S. application Ser. No. 13/133,987, filed Aug. 10, 2011 as the US National Stage entry of International Application No. PCT/US2009/067697, filed Dec. 11, 2009, which claims priority to U.S. Provisional Appl. No. 61/121,809, filed Dec. 11, 2008, the disclosures of each are incorporated herein by reference in their entirety.

STATEMENT AS TO RIGHTS TO INVENTIONS MADE UNDER FEDERALLY SPONSORED RESEARCH OR DEVELOPMENT

This invention was made with Government support under Grant No. HG004130 awarded by the National Institutes of Health. The Government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file SEQTXT_84424-904019.txt, created on Mar. 28, 2014, 13,846 bytes, machine format IBM-PC, MS-Windows operating system, is hereby incorporated by reference.

BACKGROUND OF THE INVENTION

Through massive parallelization and miniaturization, the throughput of DNA sequencing has been increased tremendously while the cost of sequencing has been reduced by several orders of magnitude compared to the conventional gel or capillary-based sequencers using the Sanger dideoxy sequencing method. Several other emerging sequencing platforms can potentially increase the throughput and reduce the cost of DNA sequencing even further by another two orders of magnitude, promising to give us the so-called $1000 genome sequencing technology (Rothberg, J. M. and Leamon, J. H., Nat Biotechnol, 26; 1117-1124 (2008); Schloss, J. A., Nat Biotechnol, 26:1113-1115 (2008); Shendure, J. and Ji, H., Nat Biotechnol, 26:1135-1145 (2008)).

The possibility of $1000 genome technologies promises to bring genomics out of the main sequencing centers and into the laboratories of individual investigators. This will dramatically transform biomedical research by enabling comprehensive analysis of genomes, transcriptomes, genetic networks and so on. Despite the great progress that has been made, the $1000 genome technology remains elusive.

The recent progress and the great challenges in genome sequencing technology development have been reported in a series of review articles (Rothberg, J. M. and Leamon, J. H., Nat Biotechnol, 26; 1117-1124 (2008); Schloss, J. A., Nat Biotechnol, 26:1113-1115 (2008); Branton, D. et al., Nat Biotechnol, 26:1146-1153 (2008)).

The invention provides improved methods for sequencing genetic materials, e.g., for medical applications and biomedical research. The disclosed methods can be applied to rapid personalized medicine, genetic diagnosis, pathogen identification, and genome sequencing for any species in the biosphere.

BRIEF SUMMARY OF THE INVENTION

The present invention provides compositions, methods, kits, and systems for rapid DNA sequencing. In some embodiments, sensors are engineered onto the surface of a polymerase molecule to monitor subtle, yet distinct, conformational changes that accompany the incorporation of each base type. Movement of one to tens of angstroms by the polymerase can be measured precisely with the Förster resonance energy transfer (FRET) technique. Multiple FRET pairs (or networks) placed at strategic residues on the polymerase can be used to monitor conformational changes in real time (10 times faster than the rate of DNA synthesis). The sensors can provide multi-parametric information about the dynamic structure of the polymerase, which in turn can provide a unique signature for each base type incorporated. Chemical modifications such as methylation on the template DNA can also be detected according to the disclosed methods.

Accordingly, the invention provides a labeled DNA polymerase wherein said DNA polymerase comprises at least one FRET donor and at least one FRET acceptor, wherein said FRET donor and FRET acceptor are positioned on the DNA polymerase so that a distinct FRET signal is generated for each different nucleotide incorporated into the new DNA strand by the DNA polymerase. The FRET donor and acceptor are positioned on the DNA polymerase so that, when the polymerase adds a nucleotide to the nascent strand of DNA, a distinct FRET signal is generated, at least depending on which base (A, C, G, T) is incorporated. In some embodiments, a distinct FRET signal is generated when the DNA polymerase reads (encounters) a methylated nucleotide on the template DNA.

In some embodiments, the FRET donor is positioned at a distance very close to the Förster radius ($R_0$) away from the FRET acceptor. For example, when the DNA polymerase is in the open position, the donor is positioned at about one Förster radius ($R_0$) from the acceptor, or within, e.g., 10, 5, 2.5, or 1 angstroms of the Förster radius ($R_0$). In some embodiments, the distance between the FRET donor and the FRET acceptor changes at least 1, 2.5, 5, 10, or more angstroms from the open position to the closed position of the DNA polymerase.

In some embodiments the FRET donor and acceptor are positioned on a solvent accessible surface of the DNA polymerase. In some embodiments, the FRET donor and acceptor do not interfere with the activity of the DNA polymerase. In some embodiments, the FRET acceptor is positioned on the finger domain, e.g., on a solvent accessible surface of the finger domain, and the FRET donor is positioned on the palm or thumb domain (or another domain that remains relatively stationary during DNA synthesis), e.g., on a solvent accessible surface of the polymerase. In some embodiments, the FRET acceptor is positioned on the thumb or palm domain of the DNA polymerase (or another domain that remains relatively stationary during DNA synthesis), e.g., on a solvent accessible surface, while the FRET donor is positioned on the finger domain, e.g., on a solvent accessible surface of the finger domain.

In some embodiments, the DNA polymerase source is selected from bacteriophage, bacteria, and yeast. In some embodiments, the DNA polymerase is a genetically engineered enzyme, e.g., a hybrid, or one from a commercial source (e.g., T7 DNA polymerase, Sequenase version 2.0™). In some embodiments, the polymerase is an RT or RNA polymerase, e.g., T7 RNA polymerase. In some embodiments, the polymerase is native or engineered reverse transcriptase, e.g., Moloney Monkey Leukemia Virus reverse transcriptase (MMLV-RT) or SuperScript III™ reverse transcriptase (Life Technologies). Examples of DNA polymerases include phi-29, Taq, T7, Klenow (*E. coli* DNA pol I large fragment), and Bst large fragment (from *Bacillus stearothermophilus* DNA pol).

In some embodiments, the DNA polymerase is phi-29, and the FRET donor and acceptor are positioned at the amino acid positions selected from those disclosed in Table 1, or within 1, 2, 3, 4, or 5 amino acids of the amino acid positions disclosed in Table 1. In some embodiments, more than one of the FRET pairs disclosed in Table 1 is included.

In some embodiments, the DNA polymerase is not phi-29, but the FRET donor and acceptor are positioned at sites that are homologous to the FRET donor and acceptor sites disclosed in Table 1 for phi-29. The homologous site can be determined by optimal structural alignment, i.e., comparison of the DNA polymerase structures.

In some embodiments, the FRET donor and acceptor both comprise a fluorescent molecule (e.g., an organic dye molecule). For example, the donor and acceptor can be independently selected from the group consisting of fluorescein, cyanine, rhodamine, and the Alexa series of dyes (Life Technologies), and the Atto series of dyes (Atto-Tec GmbH). In some embodiments, the FRET donor and acceptor both comprise fluorescent quantum nanoparticles (e.g., silver or gold nanoclusters).

In some embodiments, the labeled DNA polymerase comprises more than one FRET donor, FRET acceptor, or FRET pair (FRET donor and acceptor). For example, a FRET network can be designed where a single FRET donor excites at least two FRET acceptors that are each in close proximity to the FRET donor. In some embodiments, each FRET pair has a different set of labels.

The invention provides methods of making the labeled DNA polymerase described herein. The invention also includes methods of making any other protein in which at least one residue is labeled with a chemical moiety (e.g., a label such as a fluorescent dye or biotin molecule, or a PNA) at a selected position(s), or at least one residue is substituted with a non-native amino acid, with or without a chemical moiety. In some embodiments, the method comprises the steps of: (i) identifying (selecting) at least one first position on the DNA polymerase to be labeled with a FRET donor and at least one second position on the DNA polymerase to be labeled with a FRET acceptor; and (ii) introducing a non-naturally occurring amino acid at each of the identified (or selected) positions, thereby making a labeled DNA polymerase. In some embodiments, the non-naturally occurring amino acid is labeled when it is incorporated, while in other embodiments, the non-naturally occurring amino acid is labeled after it is incorporated into the protein.

In some embodiments, the non-naturally occurring amino acid at the first position is different than the non-naturally occurring amino acid at the second position. In some embodiments, the non-naturally occurring amino acid is labeled, e.g., with biotin, a chemically reactive group (e.g., to covalently link a dye molecule), or a fluorescent dye. In some embodiments, the non-naturally occurring amino acid is one that is not normally found in that position on the DNA polymerase, i.e., a mutated, substituted, or derivative amino acid. In some embodiments, the mutated amino acid is one with a reactive side group, e.g., cysteine or lysine.

In some embodiments, the introducing step comprises in vitro (i.e., a cell-free) translation of the DNA polymerase. In some embodiments, the introducing step comprises cell-based translation of the DNA polymerase. In some embodiments, the non-naturally occurring amino acid is labeled with the FRET donor or acceptor molecule (e.g., a fluorophore) after translation of the DNA polymerase, thereby forming a labeled DNA polymerase. In some embodiments, the non-naturally occurring amino acid comprises a FRET donor or FRET acceptor that is directly introduced into the DNA polymerase during translation.

In some embodiments, the in vitro translation reaction comprises the steps of: a) immobilizing a polynucleotide sequence (e.g., an mRNA) encoding a labeled DNA polymerase on a substrate; b) contacting said immobilized polynucleotide with two or more different translation reaction mixes in series (separately) under conditions appropriate for translation; c) washing said immobilized polynucleotide between contact with each different reaction mix; and d) repeating steps b) and c) until the DNA polymerase is translated. In some embodiments, the in vitro translation reaction comprises the steps of: a) immobilizing a polynucleotide sequence encoding a labeled DNA polymerase on a substrate; b) contacting said immobilized polynucleotide with at least one first in vitro translation reaction mix under conditions appropriate for translation; c) washing said immobilized polynucleotide; d) contacting said immobilized polynucleotide with at least one second in vitro translation reaction mix under conditions appropriate for translation, wherein said first and second in vitro translation reaction mixes are different; e) washing said immobilized polynucleotide; and f) repeating steps b)-e) until the DNA polymerase is translated. In some embodiments, at least some of the individual components of the reaction mix are added separately to the polynucleotide. In some embodiments, the wash step effectively removes the components of the reaction mix from the polynucleotide. In some embodiments, the wash step effectively removes the components of the reaction mix from the polynucleotide except for the ribosomes and tRNAs with the nascent polypeptide covalently attached and bound to the ribosome (in the P site).

In some embodiments, the at least one first in vitro translation reaction mix is selected from (i) a reaction mix comprising a non-naturally amino acid, and no other amino acids; and (ii) a reaction mix comprising all the amino acids in the labeled DNA polymerase sequence except for the non-naturally occurring amino acid. In some embodiments, the at least one second in vitro translation reaction mix is selected from (i) a reaction mix comprising a non-naturally amino acid, and no other amino acids; and (ii) a reaction mix comprising all the amino acids in the labeled DNA polymerase sequence except for the non-naturally occurring amino acid.

In some embodiments, at least one first in vitro translation mix is selected from (i) a reaction mix comprising only one tRNA species pre-charged or activated with (covalently conjugated to) an amino acid or a non-naturally occurring amino acid (e.g. labeled or non-native), and all other components essential for in vitro translation (e.g., ribosomes, GTP, elongation factors, termination release factors); and (ii) a reaction mix containing all tRNA species pre-charged or activated with (covalently conjugated to) the other naturally genetically encoded 19 amino acids, and all other components essential for in vitro translation, but no tRNA molecules for the amino acid in (i). In some embodiments, at least one second in vitro translation mix is selected from (i) a reaction mix comprising only one tRNA species pre-charged or activated with (covalently conjugated to) an amino acid or a non-naturally occurring amino acid (e.g. labeled or non-native), and all other components essential for in vitro translation (e.g., ribosomes, GTP, elongation factors, termination release factors); and (ii) a reaction mix containing all tRNA species pre-charged or activated with (covalently conjugated to) the other naturally genetically encoded 19 amino acids, and all other components essential for in vitro translation, but no tRNA molecules for the amino acid in (i).

In some embodiments, the in vitro translation is performed using an automated system. In some embodiments, the system includes a column comprising the substrate. In some embodiments, the system comprises tubing, pumps and valves for automated delivery of reaction components and wash solutions.

The invention provides methods of sequencing a DNA molecule, wherein the method comprises the steps of (i) contacting a labeled DNA polymerase with a DNA template, wherein said DNA template is hybridized to a primer; (ii) adding a DNA sequencing (synthesis) reaction mix under conditions appropriate for DNA polymerization; and (iii) detecting the identity of each nucleotide incorporated into the new strand of DNA by detecting the FRET signal generated by the labeled DNA polymerase, thereby sequencing the DNA molecule. In some embodiments, at least some of the individual components of the DNA sequencing reaction mix are added separately.

The invention provides methods of sequencing a DNA molecule, wherein the method comprises the steps of (i) contacting a labeled RNA polymerase with a DNA template, wherein a promoter sequence for the RNA polymerase is added to the said DNA template; (ii) adding a RNA sequencing (synthesis) reaction mix under conditions appropriate for RNA polymerization in the transcription process; and (iii) detecting the identity of each nucleotide incorporated into the new strand of RNA by detecting the FRET signal generated by the labeled RNA polymerase, thereby sequencing the DNA molecule. In some embodiments, at least some of the individual components of the RNA sequencing reaction mix are added separately.

The invention provides methods of sequencing a RNA molecule, wherein the method comprises the steps of (i) contacting a labeled reverse transcriptase with a RNA template, wherein said RNA template is hybridized to a primer; (ii) adding a RNA sequencing (synthesis) reaction mix under conditions appropriate for RNA polymerization in the reverse transcription process; and (iii) detecting the identity of each nucleotide incorporated into the new strand of RNA by detecting the FRET signal generated by the labeled RNA polymerase, thereby sequencing the RNA molecule. In some embodiments, at least some of the individual components of the RNA sequencing reaction mix are added separately.

In some embodiments, the labeled DNA polymerase (or RNA polymerase or reverse transcriptase) is immobilized on a substrate, e.g., in ordered arrays on a substrate. In some embodiments, the DNA or RNA template is immobilized on a substrate, e.g., in ordered arrays on a substrate. In some embodiments, the primer comprises modified nucleic acids, or peptide nucleic acids (PNA), that are nuclease resistant. In some embodiments, the DNA template is a circular molecule.

In some embodiments, the DNA or RNA template is attached to the substrate at more than one site. For example, each end of the template can be attached (i.e., anchored) to the substrate. In some embodiments, the template is stretched with each end attached to the substrate. In some embodiments, more than one labeled DNA polymerase (or RNA polymerase or reverse transcriptase) is used to sequence the entire length of the DNA molecule. In some embodiments, the method further comprises washing the immobilized DNA or RNA template, and repeating steps a)-c). In some cases, the first labeled DNA polymerase (or RNA polymerase or reverse transcriptase) is washed away after a predetermined period (e.g., after a certain number of detection events, or certain length of time). In some embodiments, several labeled DNA polymerases (or RNA polymerases or reverse transcriptase enzymes) are used, washed away (removed), and replaced during the process of sequencing the DNA or RNA molecule.

The invention provides kits and reaction mixes for carrying out the disclosed methods. In some embodiments, the kit is designed for sequencing a DNA molecule, and comprises a labeled DNA polymerase and optionally reagents for sequencing (e.g., nucleotides and buffers). In some embodiments, the labeled DNA polymerase is immobilized on a substrate. In some embodiments, the kit includes instructions for use. In some embodiments, the kit comprises a DNA sequencing reaction mix, or components thereof (e.g., dNTPs, salt and buffer components). In some embodiments, the kit is designed for sequencing an RNA molecule, and comprises a labeled reverse transcriptase and reagents for reverse transcription, such as nucleotides and buffers.

In some embodiments, the invention provides a kit for labeling a DNA polymerase, said kit comprising a polynucleotide encoding a DNA polymerase and instructions for use. In some embodiments, the polynucleotide is immobilized on a substrate. In some embodiments, the kit further comprises at least one in vitro translation mix. In some embodiments, the at least one in vitro translation mix comprises a non-naturally occurring amino acid, and no other amino acids. In some embodiments, the at least one in vitro translation mix comprises all of the amino acids except the non-naturally occurring amino acid. In some embodiments, the kit further comprises tRNAs. In some embodiments, the kit further comprises at least two FRET dyes. In some embodiments, the FRET dyes are in separate, opaque containers to avoid photobleaching.

The invention provides apparatuses and systems for carrying out the methods described herein. In some embodiments, the system comprises a labeled DNA polymerase and optical instrumentation capable of detecting a FRET signal from a single molecule (i.e., template polynucleotide). In some embodiments, the system comprises a microfabricated flow-cell with a prefabricated chip, microfluidics, temperature control, and an imaging window to detect signal. In some embodiments, the system for READS does not include the labeled DNA polymerase, but comprises the optical instrumentation, and optionally, computer software for analyzing the data. In some embodiments, the labeled DNA polymerase is immobilized on a substrate included with the system (e.g., a glass coverslip or silicone array material). In some embodiments, the optical instrumentation includes lasers and filters for use with particular FRET dyes, e.g., that emit within a desired wavelength. In some embodiments, the optical instrumentation includes an epifluorescence microscope. In some embodiments, the system comprises a computer and/or computer software for analyzing READS data.

DETAILED DESCRIPTION OF THE INVENTION

Overview of READS—a Fourth Generation Sequencing Technology

The present invention provides a method for direct sequencing of single DNA molecules. The method is called READS Genome Technology (READS: REAl-time DNA Sequencing from sngle molecules using chemomechanical nanosensor). The sequence of a DNA or RNA molecule is determined by monitoring in real time the dynamic conformational changes of the DNA or RNA polymerase as each base is incorporated into the nascent strand extending from a primer hybridized to the template strand. The unique signature of the dynamic conformational changes of the DNA or RNA polymerase as a result of the incorporation of a base type is measured by monitoring the dynamic interaction of one pair or a network of fluorescent dyes or nanoparticles using Förster/Fluorescence Resonance Energy Transfer (FRET) technique. The FRET dye molecules are attached to the appropriate residues on the surface of the polymerase protein or protein complex. Those residues can be pre-existing residues with appropriate functional groups such as primary amine, carboxylate or sulphur hydryl groups, or can be introduced into the polymerase by protein engineering. The FRET signal(s) from the individual polymerase can be detected in parallel at high-speed using total internal reflection microscopy with an electron multiplying charged coupled device (EMCCD) and laser excitation. The individual fluorescence signals of different wavelengths can be split by multi-choric beam splitters and filters and detected with 2 or more cameras.

The present invention enables high-speed and accurate sequencing of single DNA molecules. Tens of thousands of bases can potentially be sequenced directly from a single DNA molecule in a matter of minutes. The invention provides the speed and accuracy of natural DNA polymerases using native nucleotides. This is an advantage over previous technologies that relied on fluorescent nucleotides, and required a polymerase that would recognize and incorporate the labeled nucleotides. The platform of the invention, which combines the sequencing method with a high-speed imaging system, thus allows for the sequencing of a whole genome very rapidly at low cost.

Figure 1:
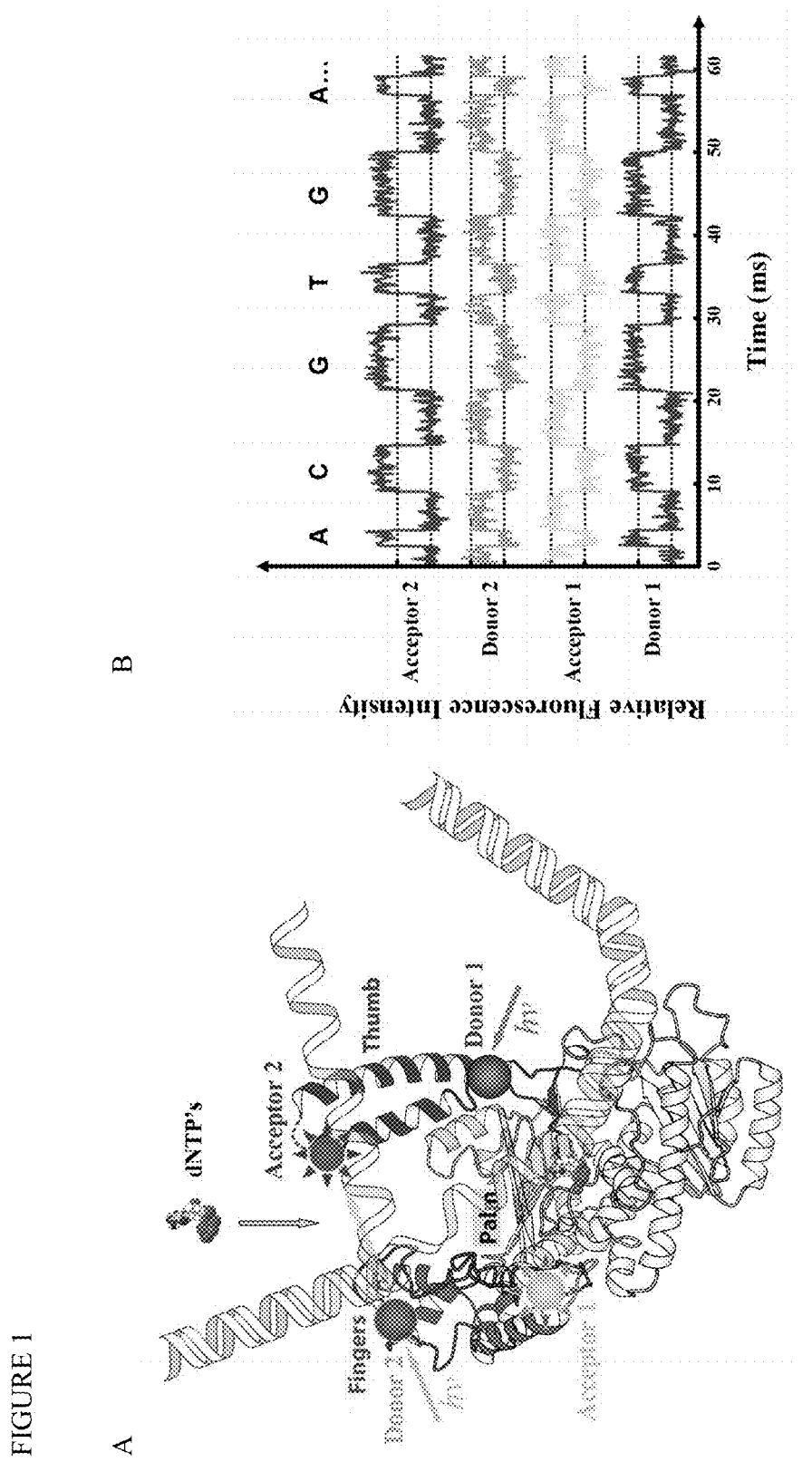
FIG. 1: Left panel: Engineered DNA polymerase with FRET pairs/network on the surface. Two pairs are illustrated, more elaborate networks can be used. Right Panel: Sequencing by monitoring the chemo-mechanical process of DNA synthesis in real time. The hypothetical signal traces show distance changes between the FRET pairs over time.

The sequencing technology of the invention provides the following advantages: (1) fast real-time sequencing; (2) direct single molecule sequencing; (3) long and accurate reads; (4) very low-cost; and (5) the capability to detect chemical modifications on genomic DNA, such as methylation, for epigenome sequencing. The basic concept is illustrated in FIG. 1.

The present invention, READS (REAl-time DNA Sequencing using chemomechanical nanosensors), incorporates the following concepts:

(1) DNA polymerase undergoes characteristic and unique dynamic conformational changes accompanying the process of binding and incorporation of each base type.
(2) The small yet unique differences of the dynamic conformational changes (with a distance change of 1-10 angstroms) in the process of incorporating each base can be precisely monitored using FRET pairs.
(3) With the current state-of-the-art imaging technology, fluorescence signals from the FRET pairs on a single DNA polymerase in real-time can be detected (10 times faster than the rate of DNA synthesis).

The FRET sensors can provide multi-parametric information about the dynamic structures of the polymerase accompanying the chemomechanical process of DNA synthesis, providing a unique signature for each base type incorporated.

Chemical modifications such as methylation on the template DNA can also be detected. Generally, C is the nucleotide that is methylated. The labeled DNA polymerases of the invention can be used to distinguish between an unmodified C and a methylated C on the template DNA strand. A slight difference in the conformation of a DNA polymerase reading a Me-C and one reading a C can result in distinct FRET signals.

Definitions

READS technology refers to REAl time DNA Sequencing using labeled DNA polymerases to detect incorporation of each nucleotide into the nascent DNA strand.

Förster resonance energy transfer (abbreviated FRET), also known as fluorescence resonance energy transfer, is a mechanism describing energy transfer between two chromophores. A donor chromophore (FRET donor), initially in its electronic excited state, can transfer energy to an acceptor chromophore (FRET acceptor), which is typically less than 10 nm away, through nonradiative dipole-dipole coupling. The energy transferred to the FRET acceptor is detected as an emission of light (energy) when the FRET donor and acceptor are in proximity (see FIG. 11). A "FRET signal" is thus the signal that is generated by the emission of light from the acceptor.

A "FRET pair" refers to a FRET donor and FRET acceptor pair.

The terms "fluorophore," "dye," "fluorescent molecule," "fluorescent dye," "FRET dye" and like terms are used synonymously herein.

A "labeled DNA polymerase" refers to a DNA polymerase comprising at least one FRET pair. The FRET donor and acceptor molecules are generally covalently attached to an amino acid on the surface of the labeled DNA polymerase. DNA polymerases share a general mechanism and structure, thus, any DNA polymerase can be designed and used according to the present invention.

The DNA polymerase "reads" the template in the 3'→5' direction, and adds individual nucleotides (bases) to the new strand in the 5'→3' direction. The polymerase requires a 3'OH group from a primer to begin extension of a new DNA strand. Individual nucleotides (dNTPs, or dATP, dCTP, dTTP, dGTP, or A, C, T, G) are added according to the general mechanism described in FIG. 3. The particular base (A, C, T, or G) depends on the sequence of the template DNA, so that the new base hybridizes to the nucleotide on the template strand through a Watson-Crick interaction. The DNA polymerase cycles between "open" and "closed" conformations. The DNA polymerase is in open position with the primer-template DNA complex. Once an incoming nucleotide enters the active site, the polymerase cycles to the closed position.

As used herein, the term "non-naturally occurring amino acid" refers to an amino acid that is attached to (labeled with) a FRET donor or acceptor, or an adaptor molecule for attaching said FRET donor or acceptor. The term also refers to an amino acid that does not naturally occur at a given site on a DNA polymerase in the native sequence of the DNA polymerase. For example, a non-naturally occurring amino acid can be an amino acid with a reactive side group which is substituted for the native (naturally occurring) amino acid at a given site on the polymerase. In this case, the FRET dye is attached to the non-naturally occurring (or substitute or mutant) amino acid in a separate step.

The term "nascent strand" refers to the new strand of DNA (or RNA) that is involved in polymerization. A DNA polymerase initially adds a first individual nucleotide (base) to a primer, adds a second individual nucleotide to the first added base, adds a third individual nucleotide to the second added base, etc., in a template strand-dependent manner. The "nascent" or "new" strand refers to the primer, the growing strand, and the strand of DNA that is polymerized by the DNA polymerase.

The term "reaction mix" refers generically to the components required for a given chemical or biological process. For example, a "translation reaction mix" will include amino acids, tRNAs, buffers, etc. as will be recognized by one of skill in the art. Similarly, a DNA synthesis reaction mix will include individual nucleotides, buffers, etc., necessary for carrying out the reaction. One of skill will appreciate that reaction mixes for DNA synthesis, transcription, and translation are well-characterized and commercially available.

The term "sequencing a DNA molecule" refers to the READS technology described herein. Sequence information is obtained for the DNA template, as well as the new and complementary DNA strand. The term DNA molecule in this context thus refers to both the template and the newly synthesized strands.

"Nucleic acid" or "oligonucleotide" or "polynucleotide" or grammatical equivalents used herein means at least two nucleotides (i.e., bases) covalently linked together. The terms "nucleotide" and "base" generally refer to individual monomers (e.g., dNTPs or rNTPs comprising adenine, thymine, cytosine, or guanine) Oligonucleotides are typically from about 5, 6, 7, 8, 9, 10, 12, 15, 25, 30, 40, 50 or more nucleotides in length, optionally up to about 100 nucleotides in length. Nucleic acids and polynucleotides are polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following amino acids can be conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. The term label as used herein generally refers to a fluorescent label, e.g., a FRET donor or acceptor. Labels can also include, e.g., an affinity agent such as biotin, chemically reactive groups, electron-dense reagents, enzymes (e.g., as commonly used in an ELISA), or digoxigenin. Any method known in the art for conjugating a label can be employed, e.g., using methods described in Hermanson, *Bioconjugate Techniques* 1996, Academic Press, Inc., San Diego.

A "labeled amino acid" generally refers to amino acids that are attached to a FRET dye (fluorescent molecule), or an adaptor molecule/linker for attachment of the FRET dye in a separate step.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA). One of skill in the art will appreciate that specific hybridization between nucleotides usually relies on Watson-Crick pair bonding between complementary nucleotide sequences.

The term "probe" or "primer", as used herein, is defined to be one or more nucleic acid fragments whose specific hybridization to a sample can be detected. A probe or primer can be of any length depending on the particular technique it will be used for. For example, primers for priming a DNA polymerase reaction (e.g., PCR) are generally between 10 and 40 nucleotides in length, while nucleic acid probes for, e.g., a Southern blot, can be several hundred nucleotides in length. The primer can be unlabeled or labeled as described below so that its binding to the target or template can be detected. The length and complexity of the nucleic acid fixed onto the target element is not critical to the invention. One of skill can adjust these factors to provide optimum hybridization conditions.

A probe or primer can also be immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) *Science* 767-773; Johnston (1998) *Curr. Biol.* 8: R171-R174; Schummer (1997) *Biotechniques* 23: 1087-1092; Kern (1997) *Biotechniques* 23: 120-124; U.S. Pat. No. 5,143,854). One of skill will recognize that the precise sequence of the particular probes can be modified to a certain degree, but retain the ability to specifically bind to (i.e., hybridize specifically to) the same targets or samples as the probe from which they were derived.

A "flowcell" or "flow channel" refers to recess in a structure which can contain a flow of fluid or gas.

A "control" sample or value refers to a sample that serves as a reference, usually a known reference, for comparison to a test sample. For example, a test sample can be an unknown sequence, and a control a known sequence. In some embodiments, the test sample can include a polymerase with an untested FRET pair, the control polymerase includes a known FRET pair.

One of skill in the art will understand which controls are valuable in a given situation and be able to analyze data based on comparisons to control values. Controls can be valuable for determining the significance of data. For example, if values for a given parameter are widely variant in controls, variation in test samples will not be considered as significant.

Basic Recombinant Methods

The invention provides routine methods of cloning polynucleotides, e.g., for expression as proteins. Polynucleotide sequences of the present invention include those that encode DNA and RNA polymerases, template polynucleotide sequences (e.g., genomic fragments to be sequenced), primers, and adaptor molecules, as described below. Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994); Kriegler, Gene Transfer and Expression: A Laboratory Manual (1990); and Current Protocols in Molecular Biology (Ausubel et al., eds., 1994-1999). Nucleic acids can be obtained through in vitro amplification methods such as those described herein and in Berger, Sambrook, and Ausubel, as well as Mullis et al., (1987) U.S. Pat. No. 4,683,202; PCR Protocols A Guide to Methods and Applications (Innis et al., eds).

One of skill will recognize that additional modifications can be made to the polymerases of the present invention without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences.

A desired protein can be obtained adopting any known genetic engineering methods for producing polypeptides (e.g., Morrison J., *J Bacteriology* 1977, 132: 349-51; Clark-Curtiss & Curtiss, *Methods in Enzymology* (eds. Wu et al.) 1983, 101: 347-62). For example, a suitable vector comprising a polynucleotide encoding the protein in an expressible form (e.g., operably linked to a regulatory sequence comprising a promoter) is prepared, transformed into a suitable host cell, and then the host cell is cultured to produce the protein.

Any commonly used promoters can be employed including, for example, the SV40 early promoter (Rigby in Williamson (ed.), *Genetic Engineering*, vol. 3. Academic Press, London, 1982, 83-141), the EF-α promoter (Kim et al., *Gene* 1990, 91:217-23), the CAG promoter (Niwa et al., *Gene* 1991, 108:193), the RSV LTR promoter (Cullen, *Methods in Enzymology* 1987, 152:684-704), the SRα promoter (Takebe et al., *Mol Cell Biol* 1988, 8:466), the CMV immediate early promoter (Seed et al., *Proc Natl Acad Sci USA* 1987, 84:3365-9), the SV40 late promoter (Gheysen et al., *J Mol Appl Genet* 1982, 1:385-94), the Adenovirus late promoter (Kaufman et al., *Mol Cell Biol* 1989, 9:946), the HSV TK promoter, etc.

Common expression vectors and host cells are commercially available. An expression vector can be introduced into host cells to express a desired sequence according to methods known in the art, for example, electroporation (Chu et al., *Nucleic Acids Res* 1987, 15:1311-26), calcium phosphate (Chen et al., *Mol Cell Biol* 1987, 7:2745-52), DEAE dextran (Lopata et al., *Nucleic Acids Res* 1984, 12:5707-17; Sussman et al., *Mol Cell Biol* 1985, 4:1641-3), Lipofectin (Derijard B, *Cell* 1994, 7:1025-37; Lamb et al., *Nature Genetics* 1993, 5:22-30; Rabindran et al., *Science* 1993, 259:230-4), etc.

A protein (or fragments thereof) can also be produced in vitro adopting an in vitro translation system. Such systems are known in the art and are commercially available (e.g., Proteinscript II™ from Ambion or Expressway™ from Invitrogen or the TNT® system from Promega, or RTS® from Roche). Cell-based methods utilizing modified tRNA molecules and tRNA synthetases can also be used. Such technologies include ReCode™ (available from Ambryx Biotechnologies), and are described, e.g., in U.S. Pat. Nos. 7,083,970 and 7,045,337.

READS Technology and Förster Resonance Energy Transfer (FRET)

DNA polymerases have precise 3-D sensors with atomic-resolution that can synthesize very long DNA molecules with high fidelity and velocity. Precise protein engineering is a much easier, cost-effective, and accessible technology than nanofabrication with semiconductor technology.

Fluorescently-labeled nucleotides are not required for READS. Thus, background resulting from the fluorescent nucleotides is not an issue. With high quality optics and imaging technique, the remaining background (e.g., resulting from Raman and Rayleigh scattering) can be suppressed to an almost negligible level. Thus, for single molecule imaging over a sustained period of time, every single photon can be counted, if desired.

Figure 2:
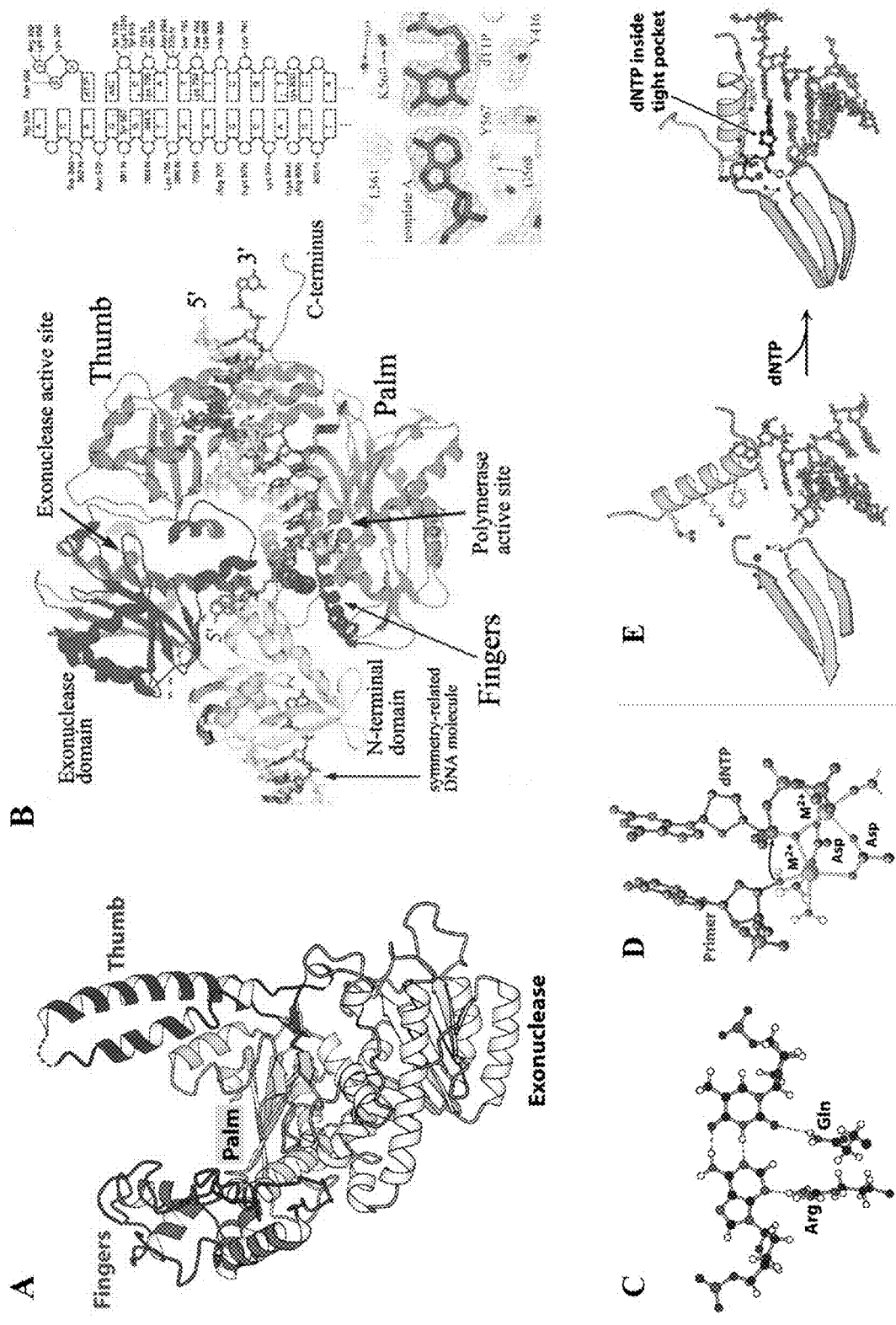
FIG. 2: (A) Right-hand structure with figures, palm and thumb subdomains. (B) A crystal structure of RB69 polymerase in the catalytically competent ternary complex (Franklin et al. (2001) *Cell* 105:657-67) (SEQ ID NO:1). (C) The specific interactions between the polymerase and primer/template (SEQ ID NOs:2-3) in the minor groove serve as the molecular ruler, guaranteeing the proper spacing between the base pairs. (D) Specific interactions between the residues on the enzyme and template/primer/nucleotide/$Mg^{2+}$ in the active site. (E) Large conformational changes accompanying the nucleotide binding and incorporation. Except (B), all other figures are from Stryer, *Biochemistry* 4$^{th}$ *ed.* (1995) W.H. Freeman & Co.
Figure 3:
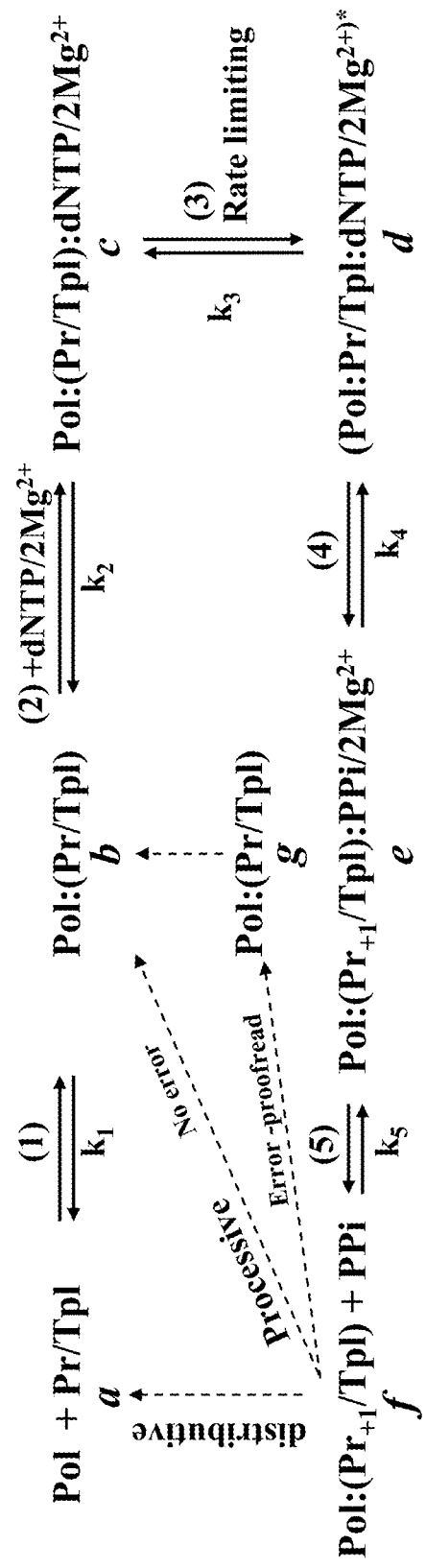
FIG. 3: Catalytic Mechanism of DNA polymerases. Conf.: Conformation; Pol: DNA polymerase; Pr: Primer; Tpl: DNA template; dNTP: one of the deoxyribonucleoside triphosphates (dATP, dCTP, dGTP or dTTP); *: catalytically competent transition state complex; PPi: inorganic pyrophosphate. There are dynamic transitions between the different conformations in the chemo-mechanical process of nucleotide incorporation.

The common catalytic mechanism of DNA synthesis for DNA polymerases is illustrated in FIG. 3. In step 1, the binding of primed DNA template to the polymerase is rapid. This begins with the specific interactions between the palm region of the polymerase and the primer/template, followed by the large movement of the thumb subdomain, which encircles the primer/template, and positions the last 3'-OH base on the primer into the active site of the polymerase (FIGS. 2B, C, D). In Step 2, the diffusion of a dNTP into the active site and subsequent binding of the dNTP trigger a rapid and large conformational change from the open position. The finger domain rotates toward the active site, and forms a tight pocket into which only a properly shaped base pair can fit (FIG. 2E). This is the closed conformation. In Step 3 (the rate limiting step), further interactions between the polymerase and the primer/template/dNTP/2Mg$^{2+}$ complex promote the complex into a catalytically competent transition state (Rothwell and Waksman, *Adv Protein Chem*, 71:401-440 (2005); Rothwell et al., *Mol Cell*, 19:345-355 (2005); Stengel et al., *Biochemistry*, 46:12289-12297 (2007)). In Step 4, the chemistry takes place: the 3'-OH group in the primer attacks the alpha phosphate group of the incoming dNTP through a SN2 reaction, resulting in the incorporation of the new base and the production of pyrophosphate. In Step 5, the complex undergoes another large conformational change. The finger subdomain rotates back to the open conformation and, concomitantly, the pyrophosphate is released, the template is translocated, and the 3'-OH is regenerated for another round of synthesis (processive synthesis) or the dissociation of the polymerase complex (distributive synthesis).

High fidelity is achieved in part due to the structural complementarities between the base pair and the enzyme active site play an important role, in addition to the specific Watson-Crick hydrogen bonding between the incoming base and the template base (McCulloch and Kunkel, *Cell Res*, 18:148-161 (2008); Kool, *Annu Rev Biochem*, 71:191-219

(2002)). An intermediate conformation has been shown to serve as an early checkpoint, allowing an incoming dNTP to preview the template, followed by rapid rejection when the bases are mismatched (Joyce et al., Biochemistry, 47:6103-6116 (2008)). From a kinetics standpoint, fidelity of the synthesis is determined by the $k_3/K_M$ of the reaction (since step 3 is the rate limiting step, $k_{cat}$ can be approximated by $k_3$) (Tsai et al., Anal Biochem (2008); Tsai and Johnson, Biochemistry, 45:9675-9687 (2006)).

In addition to the numerous conformational changes associated with the process, each step has characteristic kinetic properties ($k_1$-$k_5$), which are detected in the present sequencing process. Each DNA polymerase has a different $K_M$ for each of the 4 dNTP's. The incorporation rate of each base type ($k_3$) is also unique for each different base type. We can thus identify each base as it is incorporated by accurately measuring the rate of incorporation. The rate for a given base type is very likely sequence-dependent and therefore may vary slightly, but the variation is smaller than the differences between the different base types. Multi-parametric information of the entire process can be obtained by monitoring the dynamic conformational changes accompanying the incorporation of each base. This will capture additional unique features associated with the incorporation of each base type in addition to the unique rate of incorporation determined by $k_3$. For example, the interactions between the bases on the template, and the DNA polymerase are extensive and specific (see, e.g., FIG. 2B). A small perturbation of the network of interactions, e.g., by the presence of a methylated base, can change the polymerase conformation and the rate of the incorporation of the incoming complementary base.

FRET has evolved into a very powerful tool for measuring nanometer-scale change in distance associated with the conformational dynamics of biomolecules and complexes, including protein folding and enzyme structural dynamics, since the initial report (Stryer and Haugland, Proc Natl Acad Sci USA, 58:719-726 (1967); Haugland et al., Proc Natl Acad Sci USA, 63:23-30 (1969))

FRET and other fluorescence techniques can be used to monitor the conformational changes and kinetics of DNA synthesis (Stengel et al., Biochemistry, 46:12289-12297 (2007); Tsai et al., Anal Biochem (2008); Tsai and Johnson, Biochemistry, 45:9675-9687 (2006); Allen et al., Protein Sci, 17:401-408 (2008); Rothwell and Waksman, J Biol Chem, 282:28884-28892 (2007)). However, previous measurements were performed with a large ensemble of molecules. The present technology relies on single molecule FRET.

Eid et al. (Science 323:133-38 (2009)) observed different average pulse width (equivalent to $k_3$) for each different nucleotide: dATP: 132±22 ms; dCTP: 91±19 ms; dGTP: 117±14 ms; dTTP: 96±10 ms. The variation of their pulse width measurement was large for each dNTP, presumably due to the fact that the DNA synthesis reaction was performed with very low concentration of dNTPs ($<<K_M$). DNA synthesis according to the present techniques is performed with high concentrations of nucleotides (equal or slightly greater than $K_M$).

With current diffraction-limited optics, imaging sensors including EMCCD (electron multiplying charged coupled device), PMT (photomultiplier tube), APD (avalanche photodiode) and imaging techniques such as confocal and total internal reflection (TIRF) microscopy, single fluorescence molecules can be imaged routinely with high speed and good signal to noise ratio (Walter et al., Nat Methods, 5:475-489 (2008)). The first experimental demonstration of single molecule FRET was reported by Ha et al., Proc Natl Acad Sci USA, 93:6264-6268 (1996). Single molecule FRET is now a standard tool used for applications including studying the conformational changes of protein folding and enzyme conformation dynamics at the single molecule level (Schuler and Eaton, Curr Opin Struct Biol, 18:16-26 (2008); Tsai and Johnson, Biochemistry, 45:9675-9687 (2006); Hanson et al., Proc Natl Acad Sci USA, 104:18055-18060 (2007); Haas, Chem phys chem, 6:858-870 (2005)).

Most organic dye molecules can output on average 1-3 million photons before they are eventually photobleached. A deep-cooled EMCCD camera can detect about 100 photons with good signal to noise (S/N). If the photon collection efficiency of the imaging system is about 10%, a few thousand measurements can be made with good S/N out of a single dye molecule before it is photobleached. Dye molecules with very good photostability are highly desirable for single molecule work. The Alexa series of dyes are some of the brightest and most photostable organic dyes available. With proper steps to prevent photobleaching by removing oxygen (e.g. with glucose oxidase/catalse system) and prevent blinking (e.g. with Trolox), up to 100,000 measurements can potentially be measured from each dye using state-of-the-art optics and detectors. The main source of noise will be Raman and other scattering, which can be limited by confining the volume of illumination.

The efficiency of Förster resonance energy transfer between a donor and an acceptor dye separated by a distance of R is given by $E=1/[1+(R/R_0)^6]$ with $R_0$ being the Förster radius of the donor-acceptor pair at which $E=\frac{1}{2}$. $R_0$ is about 50-60 Å for some commonly used dye pairs (e.g., Cy3-Cy5). This distance is comparable to the size of the DNA polymerases. FRET signal varies as the distance to the $6^{th}$ power. If the donor-acceptor pair is positioned around $R_0$, a small change in distance ranging from 1 Å to 50 Å can be measured with the greatest signal to noise. With current technology, 1 ms or faster parallel imaging of many single FRET pairs is achievable. Both large and small conformational changes can be monitored with one or more FRET pairs positioned at the proper distance, in particular on the fingers and thumb subdomains.

Furthermore, the rate of in vitro DNA synthesis with some of the common DNA polymerases such as the Klenow and phi-29 DNA polymerase is slower than 100 bases/s, with the rate of synthesis by phi-29 DNA about 50-100 bases per second at 32° C. and as low as 5 bases per second at 4° C. We can thus control the rate of synthesis to 50 bases/s, and obtain 10 FRET data points per base incorporated using a 2 ms sampling rate (500 Hz). With 2×2 binning, the 1 megapixel EMCCD camera has a readout rate of 140 frames/s. With a 4 camera set up, the combined throughput of the cameras would be 560 frames/s. This can give enough FRET kinetics information to fingerprint each base type. The rate of DNA synthesis can be slowed down to 20 bases/s if necessary. Even with this speed, a 10,000-base long DNA can be sequenced in less than 10 minutes. This technology uses micro and nanofabricated arrays for efficient imaging, for example, 9 pixels per template (Barbee and Huang, Anal Chem, 80:2149-2154 (2008)). With that capability, a human genome can be sequenced in under one hour [(1,000,000/9)*20*3600=7.2 billion bases].

Polymerases for Use in READS

DNA (and RNA) polymerases are molecular motors that direct the synthesis of DNA (and RNA) in a template specific manner from individual bases/nucleotides. The structures and enzymatic mechanisms are among the best characterized of almost all proteins, and frequently used as textbook examples for enzyme catalysis and specificity.

For simplicity, we refer to DNA synthesis, and sequencing using a DNA polymerase. However, the methods of the invention can be extended to detect sequences using an RNA polymerase or reverse transcriptase, i.e., where the RNA polymerase or reverse transcriptase are labeled with a FRET pair as described for DNA polymerases.

All DNA polymerases have a common architectural framework consisting of the fingers, palm, and thumb subdomains, and sometimes an exonuclease subdomain (see FIG. 2). Despite the sequence diversity of the numerous DNA polymerases existing in nature, the structures and catalytic mechanisms share common features (Rothwell, P. J. and Waksman, G., *Adv Protein Chem*, 71:401-440 (2005); McCulloch, S. D. and Kunkel, T. A., *Cell Res*, 18:148-161 (2008)). The common mechanism for DNA polymerases is explained above and illustrated in FIG. 3 (Rothwell, P. J. and Waksman, G., *Adv Protein Chem*, 71:401-440 (2005); McCulloch, S. D. and Kunkel, T. A., *Cell Res*, 18:148-161 (2008)).

As explained above, DNA polymerases operate according to a general mechanism. Thus, any polymerase can be used in the present READS technology. Ideally, the selected polymerase
1. is easily expressed (e.g., in *E. Coli* and/or by in vitro transcription/translation systems);
2. has strong strand-displacement activity;
3. has high fidelity and processivity; and
4. has strong binding affinity to primed DNA template (i.e., a very small $K_M$ for template binding).

Depending on the assay design, error proofreading activity (i.e., exonuclease activity) can be undesirable. The exonuclease activity can act on the primer, thereby complicating the initiation of the polymerization. There are at least two ways to address this: (i) provide a primer that is nuclease resistant (e.g., modified nucleic acids or PNAs) or (ii) use a genetically engineered polymerase with reduced exonuclease activity.

A variety of polymerases can be used as at least a portion of the labeled polymerase of the invention. At least five families of DNA-dependent DNA polymerases are known, although most fall into families A, B and C. Most family A polymerases are single chain proteins that can contain multiple enzymatic functions including polymerase, 3' to 5' exonuclease activity and 5' to 3' exonuclease activity. Family B polymerases typically have a single catalytic domain with polymerase and 3' to 5' exonuclease activity, as well as accessory factors. Family C polymerases are typically multi-subunit proteins with polymerizing and 3' to 5' exonuclease activity. In *E. coli*, three types of DNA polymerases have been found, DNA polymerases I, II, and III (analogous to family A, B, and C, respectively). In eukaryotic cells, three different family B polymerases, DNA polymerases α, δ, and ε are implicated in nuclear replication, and a family A polymerase, polymerase γ, is used for mitochondrial DNA replication. Other types of DNA polymerases include phage polymerases. Any of these polymerases, combinations of all or portions of these polymerases, as well as chimeras or hybrids between two or more of such polymerases or their equivalents can be used to form a portion or all of the polymerase domain of hybrid polymerases of the invention.

Examples of DNA polymerases that can be used include without limitation: phi-29, Taq, T7, *E. coli* Klenow (from DNA pol I), *E. coli* DNA pol III, and *Baccilus stearothermophilus* (Bst) DNA pol. The DNA polymerase can also be genetically engineered, e.g., a hybrid (e.g., Phusion DNA polymerase in which a domain with strong dsDNA binding affinity is fused to a DNA polymerase to enhance processivity). Many useful DNA polymerases are commercially available (e.g., T7 DNA pol, Sequenase version 2.0™). Highly processive polymerases include phi29 and T7 DNA polymerases, and Moloney murine leukemia virus (M-MLV) reverse transcriptase. One of skill in the art will appreciate that DNA polymerases are structurally similar, and that recombinant, hybrid polymerases can be engineered using homologous domains from different polymerases.

For convenience, we have selected a polymerase that also has extensive structural data available, and few native cysteine residues on its surface. There are 780 entries of high resolution structures of DNA polymerases and DNA polymerase/substrate complexes in the protein data bank (RCSB PDB). In addition, mechanisms of many DNA polymerases have been studied extensively and elucidated in great detail. We selected phi 29 DNA polymerase because it has the desired criteria. High resolution X-ray crystal structures are available for this polymerase with and without primer/template/nucleotide substrates (Berman et al. (2007) *EMBO J.* 26:3494-3505).

Phi-29 DNA polymerase has very high fidelity (<1 error in one million bases), strong strand displacement, and high processivity (up to 100,000 bases) compared to other commonly used DNA polymerases. The conformational changes involved in the chemo-mechanical process of DNA synthesis by phi 29 DNA polymerase are known. Berman et al. solved four crystal structures of phi 29 DNA polymerase in complexes including (1) polymerase bound to a primer-template substrate (binary complex) in the post-translocated state (f in FIG. 3); (2) polymerase bound to a primer-template substrate (binary complex) before the next incoming nucleotide binds to the polymerase state (b in FIG. 3); (3) polymerase bound to two different primer-template structures with their complementary incoming nucleotides (ternary structure) (c and/or d in FIG. 3); (4) polymerase bound to single-stranded DNA (g in FIG. 3).

Labels and Dyes for Use in READS

A range of dyes can be used as FRET donors and acceptors (for reviews, see Walter et al. (2008) *Nat Methods* 5:475-89; Ha (2001) *Methods* 25:78-86; Joo et al. (2008) *Ann. Rev. Biochem* 77:51-76; Roy et al. (2008) *Nat Methods* 5:507-16). Ideally the dyes are:
1. photostable;
2. bright (with high extinction coefficients for absorption and high quantum yields for emission);
3. photochemically uniform, showing very little fluctuation in emission on the time-scale of our measurement (no blinking);
4. small (to minimize structural perturbation); and
5. excitable using available light sources and detectable using commercially available EMCCD cameras.

A variety of dyes can be used, and are known in the art. The most common ones are fluorescein, cyanine dyes (Cy3 to Cy7), rhodamine dyes (e.g. rhodamine 6G), the Alexa series of dyes (Alexa 405 to Alexa 730). Some of these dyes have been used in FRET networks (with multiple donors and acceptors). Optics for imaging all of these require detection from UV to near IR (e.g. Alex 405 to Cy7), and the Atto series of dyes (Atto-Tec GmbH). The Alexa series of dyes from Invitrogen cover the whole spectral range. They are very bright and more photostable than other dyes.

Example dye pairs for FRET labeling include Alexa-405/Alex-488, Alexa-488/Alexa-546, Alexa-532/Alexa-594, Alexa-594/Alexa-680, Alexa-594/Alexa-700, Alexa-700/Alexa-790, Cy3/Cy5, Cy3.5/Cy5.5, and Rhodamine-Green/Rhodamine-Red, etc. Fluorescent metal nanoparticles such as silver and gold nanoclusters can also be used (Richards et al. (2008) *J Am Chem Soc* 130:5038-39; Vosch et al. (2007) *Proc Natl Acad Sci USA* 104:12616-21; Petty and Dickson (2003)

J Am Chem Soc 125:7780-81). While these nanoparticles have good photostability, they are larger than other dyes, and can interfere with the function of the DNA polymerase.

Filters, dichroics, multichroic mirrors and lasers affect the choice of dye. In our examples, we selected Alexa 405, Alexa 488, Alexa 532, Alexa 568 and Alexa 680, starting with one pair or two independent pairs.

High-performing organic dye molecules can be excited to emit 1-3 million photons before they are photobleached. Highly photostable dyes are thus desired for single molecule work. The Alexa series of dyes are some of the brightest and most photostable dyes available. Removal oxygen (e.g. with glucose oxidase/catalse system) and prevention of blinking (e.g. with Trolox) will reduce photobleaching so that about 100,000 measurements can be acquired.

Selection of Sites for Labeling

Another issue is the selection residues on the polymerase to label with the FRET dyes. In the simplest model, the polymerase is labeled with one FRET pair (i.e., one donor and one acceptor), but improved instrumentation can allow for additional FRET pairs and more refined detection.

Two of the 5 steps involved in the incorporation of each base produce very large conformational changes: steps 2 and 5 (see FIG. 3). The other steps involve more subtle changes in the protein structure. In the simplest scenario, where each base type has distinguishable kinetics of conformational changes, the real-time signal from one FRET pair (intensity as a function of time, see FIG. 1) is sufficient to decode the four different bases. For example, if the difference between the $k_3$ (the rate limiting step) of each base type is large enough, a characteristic period in the signal trace of the FRET pair is observed. Where the characteristic conformational changes associated with each different base are subtle and/or sequence-context dependent, multiple networks of FRET pairs can be used.

Figure 11:
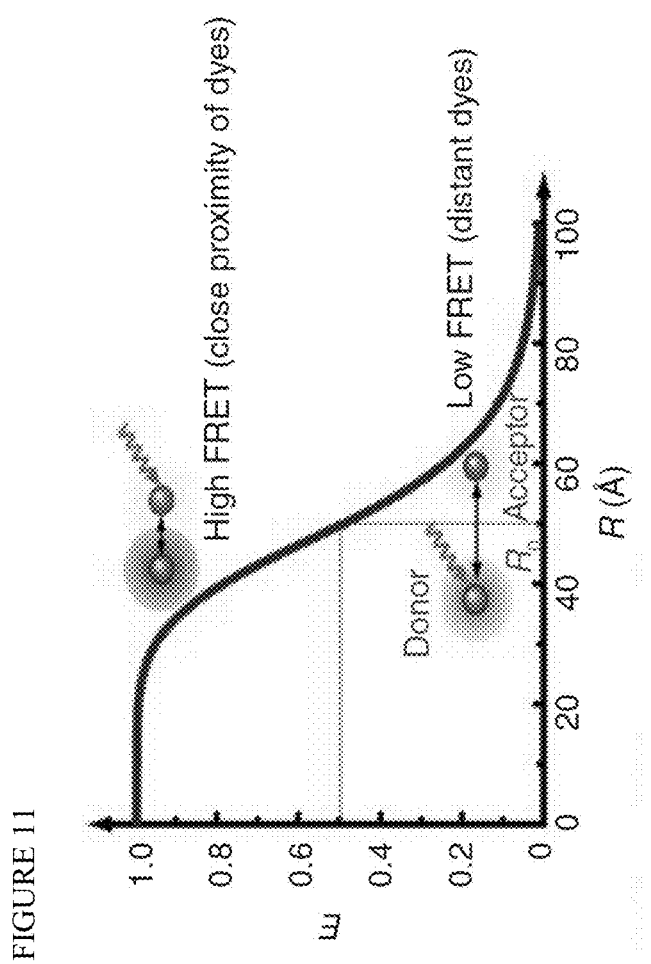
FIG. 11: Efficiency of FRET as a function of separation between the donor and acceptor. $E=1/[1+(R/Ro)^6]$; Ro: Förster radius of the donor-acceptor pair at which $E=\frac{1}{2}$. The figure is from Roy et al. (2008) *Nat Methods* 5:507-16.

Locations for positioning the FRET pairs or network on the polymerase can be judiciously selected based on the criteria described herein. To maximize detection of subtle changes, the FRET pairs are positioned at a distance roughly equal to the Förster radius between the donor and acceptor. As illustrated in FIG. 11, the efficiency of Förster resonance energy transfer between a donor and acceptor dyes separated by a distance of R is given by $E=1/[1+(R/R_0)^6]$ with $R_0$ being the Förster radius of the donor-acceptor pair at which $E=\frac{1}{2}$. $R_0$ is about 50-60 Å for some commonly used dye pairs (e.g. Cy3-Cy5). The Förster radius for any FRET pairs can be estimated using the following equation:

$$R_0^6 = \frac{9 \ln 10}{128\pi^5} \frac{\kappa^2 \eta_f}{N_A n^4} \int F(\lambda)\varepsilon(\lambda)\lambda^4 d\lambda$$

$N_A$ is Avogadro constant; n index of refraction; $F(\lambda)$ fluorescence spectrum of donor, normalized according to $\int F(\lambda) d\lambda=1$; $\varepsilon(\lambda)$ extinction coefficient of acceptor; $\lambda$ wavelength.

The FRET signal thus varies inversely as a function of the distance to the $6^{th}$ power. As can be seen in FIG. 11, the slope is steepest at $R=R_0$. Therefore, if the donor-acceptor pair is positioned around $R_0$, a small change in distance ranging from 1 Å to 10 Å can be measured with the greatest change in FRET signal.

Every DNA polymerase has a different affinity (i.e. $K_M$) and rate of incorporation (approximated by $k_3$, step 3 in FIG. 3), for each of the four different nucleoside triphosphates (dATP, dCTP, dGTP and dTTP). The rate of incorporation for each different dNTP provides the most informative characteristic signature. Thus, at least one FRET pair is designed to monitor this with maximum sensitivity. Two residues, one on each secondary structure or subdomain of the polymerase, are selected such that the distance between the donor and acceptor is equal to their Förster radius when the conformation of the two secondary structures or subdomains is halfway between the open and closed states (e.g. between b and c, or d and e in FIG. 3).

The FRET pair for monitoring any particular conformational changes, on any particular polymerase, can be positioned according to this rationale to provide maximum sensitivity and signal to noise. Following the principles described herein, one of skill can identify potential targets for mutation and labeling.

The residues to be labeled with FRET pair(s) can be determined by at least the following criteria:
1. located on the solvent accessible surface of the protein;
2. side chains orientated toward the solvent (to ensure accessibility for labeling and to minimize the perturbation of the protein structure and activity);
3. large movement between the steps of the DNA synthesis process; and
4. spaced within the ideal distance to give maximal change in the FRET signals.

The size of the dye and length of the linker (if present) should be taken into account to give an approximation of the potential change in distance between the dyes. Where a linker is used to attach the dye molecule to the protein, the distance may need to be fine-tuned to avoid excessive rotation or lateral movement. Linkers for attaching a dye to an amino acid are known and commercially available. Such linkers include simple alkyl change (e.g., propyl), oligo glycol (PEG), or linkers with more rigid structure such as a benzyl or cyclohexyl group.

Activated functional groups for linkage include but are not limited to maleimide for specific reaction to a —SH group (e.g., on cysteine) and NHS ester group for specific reaction with a primary amine (e.g., on lysine).

If necessary, the sites selected for labeling can be mutated via site-specific mutagenesis using either conventional molecular biology techniques, and labeling can be performed after the expression and folding of the proteins.

Exemplary FRET pairs and labeling sites for phi-29 DNA polymerase are described in Example 1. The positions disclosed in Table 1 are only examples; some variability is acceptable. The FRET donor and acceptor sites can be located in different positions as long as they generally follow the criteria disclosed herein. For example, the donor or acceptor can be positioned 1, 2, 3, 4, or 5 amino acids away from the sites disclosed in Table 1. The donor and acceptor sites can also be switched.

One of skill will appreciate that the sites disclosed for labeling phi-29 DNA polymerase can be applied to other DNA polymerases by optimally aligning the polymerase structures. Structural data is available for a number of DNA polymerases. One of skill can use the criteria described herein to select appropriate labeling sites (e.g., solvent accessible, outside the active site, etc.).

Detailed structural information for a number of DNA polymerases are available in the NCBI Structural database (MMDB and PDB, available at the NCBI website at ncbi.nlm.nih.gov/sites/entrez?db=Structure&itool=toolbar). For example, the structure of BST DNA Pol I can be found in the NCBI Structural database (PDB accession 3EZ5 and 3EYZ). The structure for the *E. coli* Klenow fragment of DNA pol I can be found at PDB accession 1KFD, 1DPI, 2KZZ, and 2KZM. The structure for high fidelity DNA Pol δ from *S.*

*cerevisae* can be found at PDB accession 3IAY. The structure for Taq DNA Pol I can be found at PDB accession 4KTQ. T7 DNA pol structure is available at PDB accession 2AJQ.

Using these structural data, positions on the specific DNA polymerase can be selected, e.g., for solvent accessibility. FRET donor and acceptor positions can be selected using the known structures to be in close proximity to each other (about 1 $R_0$), with detectable change in proximity during DNA synthesis.

Methods of Making Labeled Polymerase

The labeled polymerases of the invention can be made according to common recombinant and labeling methods. For example, amino acid residues that are easily linked to dye molecules (e.g., directly, through a secondary label such as biotin, or through a linker) can be introduced into the sequence of the polymerase as described above. Such residues include cysteine, lysine, arginine, aspartate, and glutamate. A labeled or modified amino acid can also be added directly to the polymerase during translation, as described herein.

The polymerase can be transcribed and translated using cell-based or cell-free expression systems. Modified amino acids can be directly introduced into a protein in a cell-based transcription/translation system that uses non-naturally occurring tRNA molecules. These modified tRNAs recognize unique codons, and can be loaded with a desired modified residue. The cells used for expression are genetically modified to express the unique tRNAs and tRNA synthetases. The cells can thus be used to express modified proteins by introducing a coding sequence with one of the unique codons. Such technologies include ReCode™ (available from Ambryx Biotechnologies), and are described, e.g., in U.S. Pat. Nos. 7,083,970 and 7,045,337.

Non-naturally occurring fluorescent amino acids can be directly incorporated to label the polymerase molecule. For example, Summerer et al. ((2006) *Proc. Natl. Acad. Sci. USA* 103-9785) describe 2-amino-3-(5-(dimethylamino)naphthalene-1-sulfonamide) propanoic acid (dansylalanine) genetically encoded in *Saccharomyces cerevisiae* using an amber nonsense codon, and a corresponding orthogonal tRNA/aminoacyl-tRNA synthetase pair.

Non-natural, fluorescently-labeled amino acids can also be incorporated using an *E. coli* in vitro translation system (Hohsaka et al. 2003 *Nuc. Acids Symp. Series* 3:271). In vitro transcription/translation systems are also commonly available, e.g., the RTS system (5Prime™), Proteinscript (Ambion®), or Expressway™ (Invitrogen™). Use of a cell free method of making labeled phi-29 polymerase is described in the examples.

Cysteine, lysine, or any other easily-labeled amino acid can be the non-naturally occurring amino acid incorporated into the DNA polymerase. In this case, non-natural refers to non-native or mutant. The selected residue can be labeled using standard methods with an organic fluorescent dye molecule. Standard reactions include: the specific reaction between a maleimide-labeled dye molecule and the sulfhydryl group on the cysteine; and the reaction between an NHS-labeled dye molecule and the amine group on Fmoc-protected lysine. If the amino acyl tRNA synthetase is not capable of activating the cysteine-tRNA or lysine-tRNA with the corresponding labeled amino acid, the labeling can be performed after charging the tRNA with the unlabeled amino acid using the tRNA synthetase. The modified cysteine and lysine charged to their cognate tRNA molecules can be efficiently incorporated into the growing peptide chain by the ribosome either in vivo or in vitro. This method allows simple labeling of a polymerase with any combination of the desired fluorescence dyes at any desired positions.

Immobilization of Labeled Polymerase

The labeled polymerase can be immobilized on a substrate for detection. In this case, template polynucleotides are added to the immobilized polymerase molecules. In some embodiments, the template DNA is pre-primed with a complementary primer before addition to the immobilized polymerase. A reaction mix that includes dNTPs (dATP, dCTP, dTTP, dGTP) can also be added. The template to be sequenced can take nearly any form, e.g., sheared genomic fragments, single- or double-stranded linear molecules, or circular molecules (e.g., plasmid DNA).

The solid substrate can be arranged, e.g., in an array on a flat surface, in a spot array, or on beads. Common substrates for this purpose include glass and quartz slides. The array format is convenient because the READS technology is designed to gather measurements from more than one DNA polymerase simultaneously.

Using the example of an array format, a wide variety of capture area sizes (spots for capturing the polymerase molecules) can be employed. The substrate can comprise wells and/or spot sizes of a predetermined size and density e.g., spot sizes of approximately 50 nl or smaller. The pattern of wells or spots can provide particular information such as bar code information. The substrate can also contain materials used to generate a reference measurement or control signal for either the assay or the signal readout, or may be simply used as a locating device on the substrate.

The polymerase can be immobilized by reacting the amine group(s) at the N-terminus or lysine residues, the side chains of the aspartic and glutamic acid residues, or the carboxylate group at the C-terminus of the polymerase with an amino or carboxyl group on the substrate, thereby forming a covalent peptide bond. Carbodiimide can be added to improve the binding reaction. Biotin or avidin can be attached to the polymerase (e.g., on a side chain of a particular amino acid by conventional methods), and avidin or biotin fixed on the substrate to effect binding. Functional groups and reactions that can be used for immobilization include:

Sulfhydryl—bromoacetyl reaction
Sulfhydryl groups (under oxidizing, alkaline conditions)
Amino—aldehyde reaction
Sulfhydryl—aldehyde reaction
Hydroxyamino—aldehyde reaction Immobilization on the substrate can also rely on physical adsorption. In this case, immobilization is attained simply by contacting the polymerase molecules in buffer solution with the substrate. The immobilization reaction may be carried out, for example, at room temperature for about 15 minutes to 2 hours, or at 4 C overnight according to conventional methods.

One of skill will appreciate that these methods can be used with an intermediate linker molecules as well. PEG is commonly used as a linker. The substrate can also be treated to improve binding of the linker or reactive group. Gold and polyelectrolyte multilayer are examples of treatments for solid substrates.

In a specific example, DNA polymerase with Streptag or biotin label can be immobilized onto a 170 µm glass coverslip coated with streptavidin and assembled in a flowcell. The surface quality of the substrate is critical for single-molecule imaging. The glass coverslip substrate is cleaned, e.g., with the RCA protocol (1:1:5 $NH_4OH:H_2O_2:H_2O$ at 70 C, followed by cleaning with piranha solution), derivatized with aminopropyltriethoxysilane, followed by NHS-PEG5000-biotin.

The biotinylated coverslip is then assembled into a flowcell. A streptavadin solution is flowed into the flow cell to saturate the biotinylated surface with streptavidin. A solution of the labeled polymerases is then flowed into the flowcell. The immobilization is monitored in real time with TIRF to ensure the proper density of the polymerase on the surface. The polymerases should be well separated (e.g., on average about 500 nm apart) for better optical resolution.

PEG5000 can be used as a long linker to separate the polymerase from the glass surface (~10-15 nm). An image is captured before DNA template is loaded onto the polymerases. A solution of the DNA templates pre-hybridized with a primer is flowed into the flowcell. After a period of incubation, another image is captured. There should be a change in the FRET intensity since the polymerase will bind to the DNA and encircle it. Finally, a solution of dNTP's is flowed into the flowcell to initiate the DNA synthesis. A series of images are taken to monitor the FRET signals A test template comprising synthetic 120-base long homopolymers can be used to establish the characteristic fingerprint associated with each different base type. Four 120-base long single-stranded DNA templates containing stretches of poly A, poly C, poly G and poly T can be constructed and used for the measurements. These test templates can be pre-hybridized with a 30-base long primer and loaded onto the polymerases as described above. Once each characteristic fingerprint is established, more complex templates can be used with READS technology, e.g., including templates with methylated bases.

Immobilized Template Polynucleotides

In some embodiments, the template polynucleotides are immobilized on a substrate. In some embodiments, the template is primed with a complementary oligonucleotide before immobilization, while in some embodiments, the primer is added after immobilization. In some embodiments, the primer oligonucleotide can perform a dual function, and be used as a capture probe to immobilize the template to the substrate. Such a dual function oligonucleotide will be attached to the substrate closer to the 5' end of the oligonucleotide, leaving the 3' end available for hybridization to the template, and the 3' hydroxyl group available for addition of nucleotide bases by the labeled polymerase. As explained above, the primer can include modified, nuclease-resistant bases, or can comprise PNA molecules.

When the template polynucleotide is immobilized, labeled DNA polymerase molecules are loaded on to the template molecules, and combined with reaction mix under conditions appropriate for DNA polymerization.

Methods of attaching nucleic acids to a substrate are known in the art. Polynucleotide molecules can be fixed to the substrate using a variety of techniques, including covalent attachment and non-covalent attachment. Indeed, many of the same techniques described above for immobilizing the polymerase can be used.

In some embodiments, the substrate includes capture probes that hybridize with the polynucleotide molecule. An adaptor oligonucleotide, e.g., between the template and capture probe, can also be used. In some embodiments, the adaptor oligonucleotide is ligated to the template, and hybridizes to the capture probe. In some embodiments, the adaptor is a polynucleotide (e.g., polyA), which can be added with a terminal transferase, and will hybridize to a capture probe. In some embodiments, capture probes can comprise oligonucleotide clamps, or like structures, that form triplexes with adaptors, as described in Gryaznov et al., U.S. Pat. No. 5,473,060.

A surface can have reactive functionalities that react with complementary functionalities on the polynucleotides to form a covalent linkage (see, e.g., Smirnov et al. (2004), *Genes, Chromosomes & Cancer,* 40: 72-77; Beaucage (2001), *Current Medicinal Chemistry,* 8: 1213-1244. Long DNA molecules (several hundred bases) can also be efficiently attached to hydrophobic surfaces, such as a clean glass surface that has a lower concentration of reactive functionalities, e.g., —OH groups.

Polynucleotide molecules can be adsorbed to a surface. In this case, the polynucleotide molecules are immobilized through non-specific interactions with the surface, or through non-covalent interactions such as hydrogen bonding, van der Waals forces, etc. Attachment may also include wash steps of varying stringencies to remove incompletely attached single molecules or other reagents.

In a specific example, we have assembled high-density arrays with near perfect order using either magnetic or electric fields (e.g., Barbee & Huang (2008) *Anal Chem* 80:2149-54). Photolithography can be used to generate a wafer-scale array of microwells in a layer of photoresist or $SiO_2$ on a chemically functionalized glass cover slip. The array is enclosed within a microfluidic device for either magnetic or electric field-directed assembly of microbeads conjugated to DNA molecules into very high-density array with virtually no background or defects. These methods are scalable for fabricating large-scale, high-density arrays tens of nanometers in dimension using well established, production-scale manufacturing processes. Such low-defect arrays are free of background and are compatible with automated processes, microfluidics devices and conventional microscopy. The highly ordered arrays, when properly sized and aligned to a given CCD sensor, can also greatly improve imaging efficiency and reduce the complexities of image processing. We have shown that as few as 3×3 pixels are required to image each feature. These techniques can improve the efficiency of our single molecule arrays and eliminate background (due to Raman and other scattering) by reducing the area of illumination. The single molecule of DNA template can be conjugated to a small particle (e.g., a silica or DNA particle with a diameter of, e.g., about 200 nm) as a carrier for immobilization.

Instrumentation

Certain embodiments of the invention pertain to a device, system, or apparatus for performing READS. The system can be specifically constructed for the present methods, or it may be a general-purpose optical instrument, selectively activated or configured by, for example, a computer program stored in the computer. The processes presented above are not inherently related to any particular optical instrument or computing apparatus.

FRET imaging systems having optics, various means for sample presentation, correction algorithms, and high-sensitivity cameras are known in the art (see, e.g., U.S. Pat. Nos. 6,661,909, 6,456,734, 7,012,694). In some embodiments, the system will comprise one or more of a microscope, a detection camera, a light source, epifluorescence cubes (e.g., for donor, acceptor, and FRET), an image processor, and an image output device to view the data.

In some embodiments, the optical instrumentation includes at least a camera and microscope. The optical instrumentation can also provide for background subtraction, spectral overlap corrections, and transformation of data from three channels. The epifluorescence cubes include filters (e.g., excitation filter, emission filter, dichroic mirror) that depend on the exciting and emitting wavelengths of the FRET dyes.

In some applications, samples are immobilized on a substrate (e.g., glass) which is directly observed by the optical system. In some embodiments, samples are fixed in a flow channel, and cast on a chip. Channels can be formed by bonding the chip to a flat substrate (e.g., a glass cover slip) which seals the channel. In this case, one side of the synthesis channel is provided by the flat substrate.

The apparatus can contain in an integrated system a flow cell in which a plurality of channels are present, and fluidic components (such as micro-pumps, micro-valves, and connecting channels) for controlling the flow of the reagents into and out of the flow cell. An apparatus of the invention can utilize plumbing devices described in, e.g., Zdeblick et al., A Microminiature Electric-to-Fluidic Valve, Proceedings of the 4th International Conference on Solid State Transducers and Actuators, 1987; Shoji et al., Proceedings of Transducers, San Francisco, 1991; Vieider et al., Proceedings of Transducers, Stockholm, 1995. In some apparatus comprises synthesis channels, valves, pumps, and connecting channels.

In some embodiments, the flowcell comprises of the coverglass substrate assembled to a glass slide or a stainless steel plate via a silicone rubber gasket with pre-patterned channels for the reaction. There are holes drilled out in the glass slide or stainless steel plate for fluidic connection. In some embodiments, the flowcell is assembled into an apparatus with precise temperature control and microfluidics, and a window for efficient fluorescence imaging.

Figure 4:
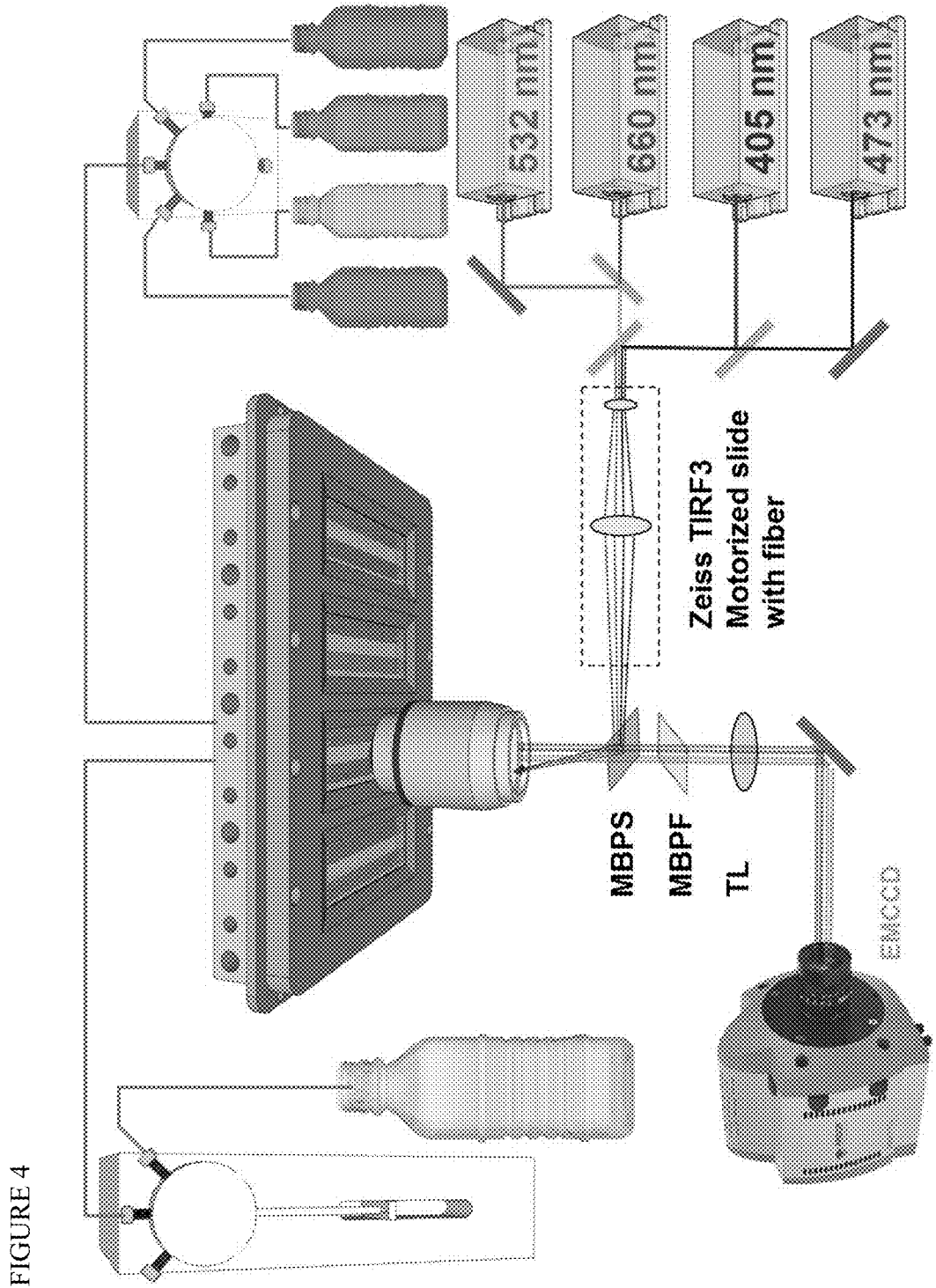
FIG. 4: Schematic of an automated system with microfluidics and TIRF for high-speed multi-color fluorescence imaging of single molecules. Objects are not drawn to scale. All components are controlled by a computer with a custom software package.

For high speed imaging, an objective-based TIRF system for multicolor, sensitive imaging of single molecules can be assembled as in FIG. 4. The system consists of an epifluorescence microscope (AxioObserver Z1 microscope, Carl Zeiss) with a TIRF slider (TIRF 3 Slider, Carl Zeiss), through which the laser excitation is introduced into the objective. The TIRF angles can be rapidly adjusted by an actuation mechanism driven by a piezo-motor. A 100x oil objective lens with a NA of 1.46 (Alpha planapo 100x/oil, Carl Zeiss) can be used for both TIR laser excitation and fluorescence detection. The system has four custom-built direct-diode and diode-pumped solid state lasers (405 nm, 488 nm, 532 nm, and 660 nm) for excitation. The laser is coupled to the TIRF slider by a polarization preserving single-mode broad-band optical fiber (KineFLEX, Point Source). Focus position can be maintained during imaging using a autofocusing system (Definite Focus, Carl Zeiss), which uses 835 nm LED light reflected off the surface of the coverslip for focus feedback. We have used the TIRF microscope to monitor incorporation of the labeled nucleotides by the DNA polymerase.

A quad-band beamsplitter and emission filter (Pinkel set, Semrock Inc.) is used so that no mechanical switching is required to acquire 4 color fluorescence images. For detection, a very sensitive frame transfer EMCCD camera is used (iXon Plus, Andor Technologies) with a high readout speed of 35 Megapixels/s, single photon sensitivity and 14-bit dynamic range. Using the pixel binning feature on the camera, full images can be acquired continuously at exposure times as low as one millisecond with 6×6 binning (36 pixels per feature). The high power (>100 mW) and high modulation rate (>100 kHz) of the solid state lasers coupled with the high readout rate of the camera allow for high SNR imaging with only one millisecond exposure time per channel. This system is capable of real-time imaging of single molecules.

Figure 5:
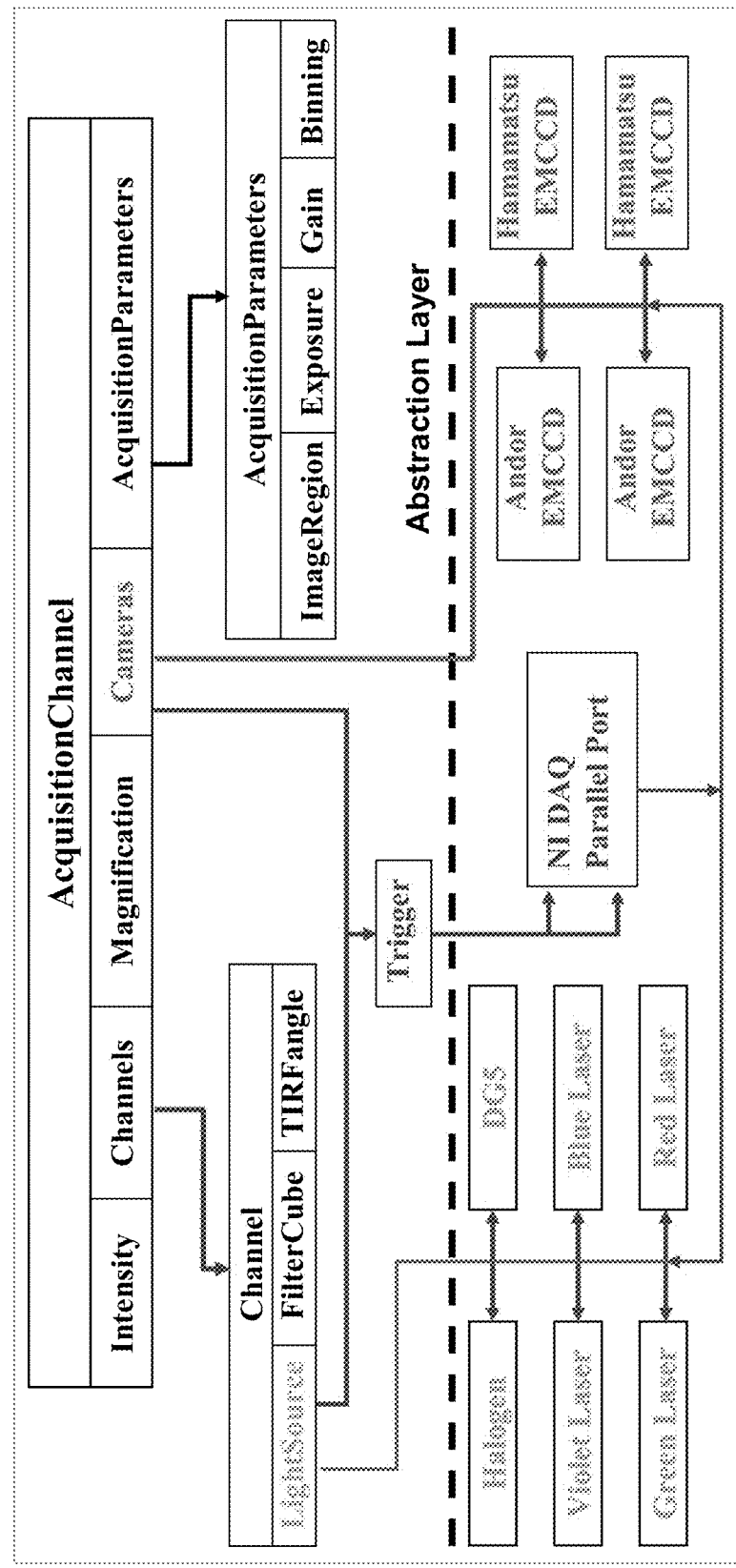
FIG. 5: Schematic of the software for automated high-speed imaging. It is of modular design, written, e.g., in C++. Hardware is abstracted from implementation for portability.

FIG. 5 shows a hierarchical structure of a small section of the system control software (written, e.g., in C++ or appropriate programming language). Using modular programming, the time from design of a sequencing protocol to implementation can be reduced. Furthermore, abstraction of the hardware from the software allows for easy integration of new devices as new technology is developed in areas such as EMCCDS and solid state lasers. Another benefit of having a custom software platform is the ability to optimize and synchronize a sequencing protocol, from reagent delivery to image acquisition, for the highest sequence throughput. Precise timing of the excitation source, TIR angle, and detector is achieved using TTL triggering from a DAQ board (PCI6733, National Instruments). This ensures minimal crosstalk between fluorescent channels and uniform light collection in every image. The control software provides a central framework for extensibility and optimization of our imaging system.

One focus is to improve the speed and efficiency of the imaging system, because these factors determine the read lengths of our imaging system. As explained above, a deep-cooled EMCCD camera can detect about 100 photons with good signal to noise (S/N) ratio. If the photon collection efficiency of the imaging system is about 10%, a few thousand measurements can be made with good S/N out of a single dye molecule before it is photobleached.

Figure 13:
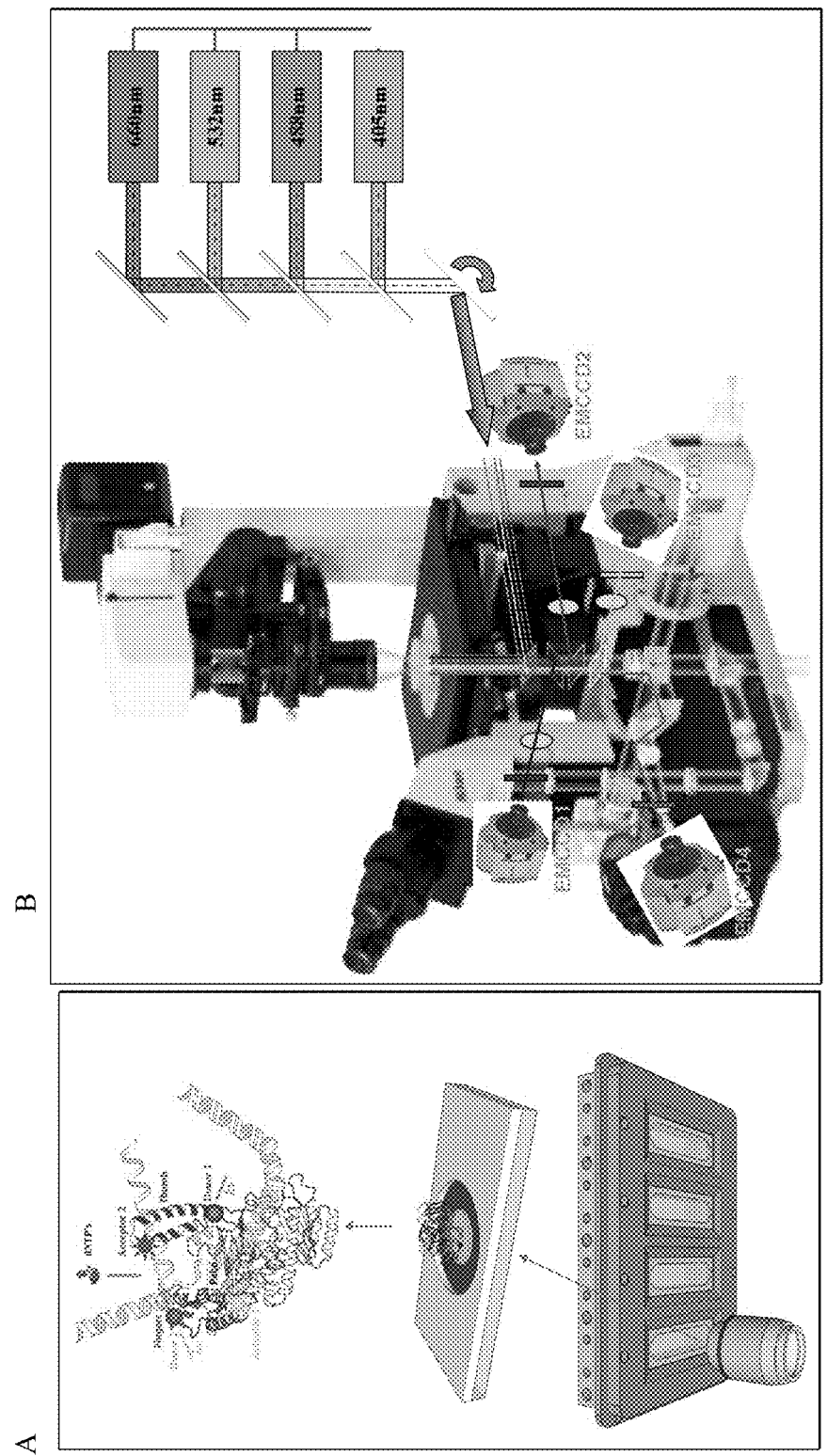
FIG. 13: A system for high-speed single molecule sequencing. Left: Flowcell and arrays of single DNA polymerases with chemo-mechanical nanosensors. Right: An imaging system with 4 cameras and 4 lasers.

Due to Raman and Rayleigh scattering, the number of photons required for good S/N may be greater and number of measurements that can be made may be lower. High quality instrumentation can be used to minimize these effects, e.g., two back-illuminated EMCCD cameras (Andor Technology or Hamamatsu Photonics) with very high QE (quantum efficiency, up to 90%) and high data rate (10 MHz/pixel without binning) Use of two cameras to monitor signal(s) from the donor(s) and acceptor(s) of the FRET pair(s) simultaneously, more snapshots of the DNA polymerase in action can be taken during the DNA synthesis. About 100,000 measurements can be made with a single Alexa dye molecule. If we assume that 10 snapshots are needed to capture the fingerprint of each base, up to 10,000 bases can be sequenced per feature. An objective lens with very high light collecting power is used for highest efficiency in photon collection, e.g., 40x/NA1.3 oil objective and 20x/NA1.0 water-immersion objective. Fast-switching high power lasers are desired for high-speed imaging. As explained above, a laser-based TIRF system can be used for high speed single molecule imaging (see FIG. 13).

We developed a software package for high-speed imaging by programming each device to enable hardware triggering. In principle, the DNA synthesis can be carried out at lower rates (e.g. 10 bases/s) for easier imaging. Reduced rate DNA synthesis can be used to capture more snapshots during the base incorporation.

Indeed, the rate of synthesis for phi-29 DNA polymerase can be varied from ~5 bases/s at 4° C. to 100 bases/s at 32° C. With a reaction rate of 5 bases per second, for example, allows up to 200 ms to take a series of snapshots of the FRET signature resulting from the chemo-mechanical process of base incorporation.

Use of a system with 4 cameras and 4 fast-switching lasers (1 MHz) for multi-parametric measurement of FRET pairs/network will give us the ability to perform more elaborate excitation patterns, and to obtain much more information rapidly. We expect good S/N with exposure times of 5 ms or less using the improved instrumentation. Using the improved system, very small perturbations in the chemo-mechanical process during DNA synthesis (e.g. the presence of a methylated base on the template DNA) can be detected.

Kits and Reaction Mixes

The present invention provides kits and reaction mixes for conducting READS technology. The components will depend on the particular aspect of READS for which it is designed (e.g., making labeled DNA polymerase, sequencing using immobilized DNA polymerase, or sequencing using immobilized template DNA). The kit will generally include instructions for conducting READS reactions using the components of the kits.

A reaction mixture for making labeled DNA polymerase can include a polynucleotide encoding the polymerase, so that the sequence can be manipulated by the customer (e.g., to add codons for non-naturally occurring amino acids). In some embodiments, the reaction mixture does not include the encoding sequence, and it is supplied by the customer to have codons for non-naturally occurring amino acids in specific positions.

In some embodiments, the reaction mixture includes components for an in vitro transcription and translation. Such components include RNA polymerase, rNTPs, various tRNA sythetases, tRNAs specific for all 20 amino acids, amino acids, and various buffers and salts. In some embodiments, there are separate reaction mixtures for each non-naturally occurring amino acid. In some embodiments, all of the non-naturally occurring amino acids to be incorporated, and the appropriate tRNAs and tRNA synthetases, are all included in the same reaction mixture. In some embodiments, the non-naturally occurring amino acids are each labeled with a FRET dye, or adaptor molecule for attaching a FRET dye. In some embodiments, the non-naturally occurring amino acid is unmodified, and will be modified (labeled) after translation of the DNA polymerase.

Kits for making a labeled DNA polymerase can include a reaction mixture as described above. In some embodiments, the kit includes a DNA polymerase, optionally comprising an adaptor sequence (e.g., biotin) for immobilization to a substrate. In some embodiments, the DNA polymerase already includes a number of non-naturally occurring nucleic acids (e.g., cysteines) that can be selected for labeling by the customer. A range of dyes can be included, and selected based on the capability of the instrument to be used.

In some embodiments, the kit will include a nucleotide sequence encoding a labeled DNA polymerase, and reagents for an in vitro or cell-based transcription/translation reaction. The nucleotide sequence can also be further manipulated by the customer, e.g., to add additional codons for non-naturally occurring amino acids. In some embodiments, the kit will include several reaction mixes for translating the DNA polymerase, in order to introduce non-naturally occurring amino acids to specific, targeted sites on the polymerase surface. In some embodiments, the non-naturally occurring amino acid is an easily labeled amino acid that is introduced to a non-native position (creating a mutant DNA polymerase). In some embodiments, the non-naturally occurring amino acid is labeled with a FRET dye. In the latter case, modified tRNAs and tRNA synthetases can also be included.

Reaction mixtures for synthesis and sequencing from an optionally immobilized template DNA can include dNTPs (dATP, dGTP, dTTP, dCTP), and various salts/buffers as required by the labeled polymerase (e.g., Mg, Mn, and Zn salts). Reaction mixtures can also include components for immobilizing a template DNA, e.g., adaptor nucleotides, biotin or avidin, etc.

Kits designed for assays using immobilized template DNA can include labeled DNA polymerase as described herein. In some embodiments, the DNA polymerase is packaged without being labeled, and instructions and reagents are included to label the polymerase to conform with the optical instrument that will be used by the customer. In some embodiments, oligonucleotides are included, e.g., capture probe, primer oligonucleotides, and/or oligonucleotides to be ligated to the template DNA sequences.

In some embodiments, the kit includes various reaction mixtures, e.g., as described above, while in some embodiments, the kit does not include reaction mixtures, and the components are packaged separately. In some embodiments, the kit will include an appropriate substrate (e.g., treated glass slides), optionally including immobilized control sequences.

Kits designed for sequencing with immobilized, labeled DNA polymerase can include reagents to immobilize the DNA polymerase (described above), or include a substrate with the labeled DNA polymerase already attached.

Kits for sequencing/synthesis can comprise components for a reaction mix. A typical DNA polymerase reaction mix can include dNTPs, buffers (e.g., Tris) various salts (e.g., KCl, NaCl, $(NH_4)_2SO_4$, $MnCl_2$, Zn salts, $MgCl_2$), and often stabilizer, detergent, DMSO, and DTT. Kits of the invention include additives to increase the specificity and efficiency of polymerase reactions.

It will be appreciated that kits of the invention also encompass any combination of the above-described components.

Instructions can be included with kits of the invention. A typical protocol for a kit, e.g., for sequencing using an immobilized template DNA, can include the following instructions:

Prepare template DNA (e.g., including isolation and removal of contaminants);

Ligate adaptor oligonucleotide sequence to the template DNA (e.g., to hybridize to a capture probe on the substrate, or to a primer sequence);

Immobilize template DNA to substrate;

Add primer oligonucleotide;

Add labeled DNA polymerase and DNA polymerase reaction mix;

Incubate at T (temperature ranges given depending on capability of imaging system and desired rate of reaction);

Detect FRET signals generated by labeled polymerase;

Optionally, stop polymerase reaction by washing away DNA polymerase and reaction mix;

Add new (non-photobleached) DNA polymerase and DNA polymerase reaction mix;

Detect FRET signals as before.

It will be appreciated that the above exemplary protocol can be varied using parameters well known in the art to optimize the conditions for efficiency and specificity of DNA polymerase activity. For example, synthesis of longer target nucleic acids may require longer incubation times and/or higher temperatures for efficient and specific amplification.

It is understood that the examples and embodiments described herein are for illustrative purposes only and that various modifications or changes in light thereof will be suggested to persons skilled in the art and are to be included within the spirit and purview of this application and scope of the appended claims. All publications, websites, patents, and patent applications cited herein are hereby incorporated by reference in their entireties for all purposes.

EXAMPLES

Example 1

Design of Labeled Phi-29 DNA Polymerase

For the sake of illustration, we describe our systematic examination of the crystals structures of phi-29 DNA polymerase complexed with various substrates. We used a genetically engineered exonuclease-deficient phi-29 DNA polymerase (Berman et al., *EMBO J*, 26:3494-3505 (2007). The mutations involved in eliminating exonuclease activity do not affect the active site, or adjacent sites on the finger, thumb, and palm domains.

One of skill will appreciate that the sites disclosed for labeling phi-29 DNA polymerase can be applied to other DNA polymerases. As explained above, the structures of DNA polymerases are well-conserved. Thus, through optimal structural alignment (alignment of amino acids present in particular structural positions), the positions disclosed herein can be ascertained for a broad range of polymerases.

We selected residues on the finger subdomain as candidate labeling sites for the fluorescence donor and some on the palm or thumb subdomains for the fluorescence acceptor.

Figure 7:
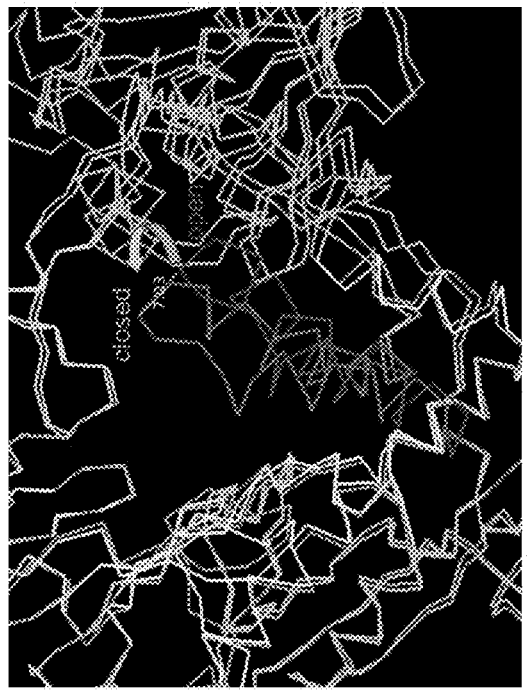
FIG. 7: Crystal structure of phi-29 DNA polymerase (SEQ ID NO:4) complexed with primer-template DNA (SEQ ID NOs:5-6). The subdomains are displayed in cartoon model: finger, palm, thumb, exonuclease, TPR1 and TPR2. The primer/template DNA are shown in stick model. The PDB ID: 2PZS file (Berman et at. (2007) EMBO J. 26:3494-3505) was used to generate the figure with the program PyMOL (available on the world wide web at pymol.org).
Figure 7:
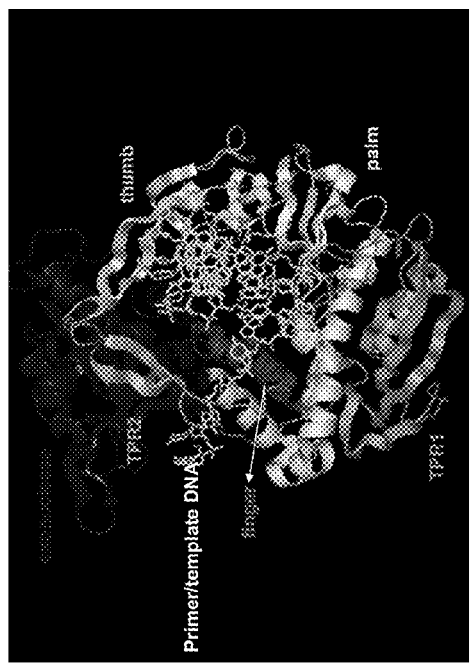
Figure 8:
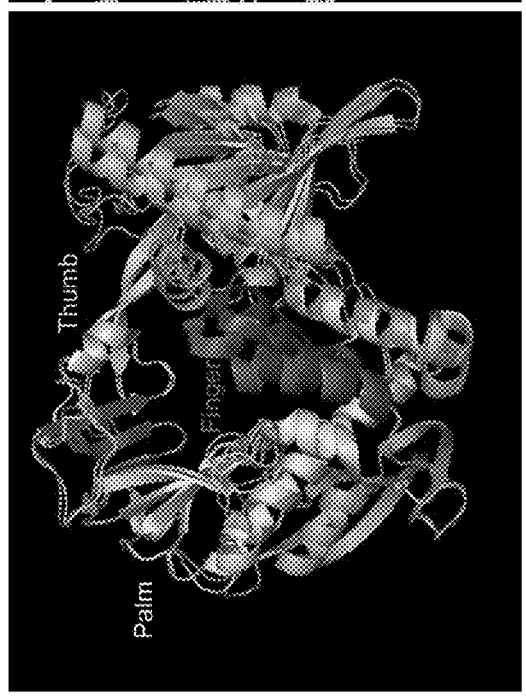
FIG. 8: Comparison of the "open" and "closed" form of phi-29 DNA polymerase (SEQ ID NO:4). Left panel: the superimposition of the "open" and "closed" forms. Right panel: Highlight of $C_\alpha$ backbone tracing in the finger subdomain.

FIG. 7 shows phi-29 DNA polymerase complexed with primer/template DNA. Although there are two Terminal Protein Region (TPR) subdomains present in the primed DNA polymerases, we have focused on the conformation and specific residues on the polymerization domain which is composed of the finger, palm and thumb subdomains. The post-translocation binary complex of phi-29 DNA polymerase complexed with primer-template DNA (PDB ID: 2PZS) and the ternary complex of polymerase complexed with primer-template DNA and incoming nucleotide substrates (PDB ID:2PYJ) are defined as "open" and "closed" conformation, respectively. The terms reflect the conformational change triggered by nucleotide incorporation. The conformational transition is compared based on $C_\alpha$ chain alignment of the palm and thumb subdomains between the open and closed complex (FIG. 8). The RMS (root-mean-squared) deviation between these two structures is 0.583 Å. Conformational change in the finger subdomain when the structure transitions between the "open" and "closed" form is very large with a 7.03 Å movement of the tip region after the binding of the incoming dNTP.

Figure 9:
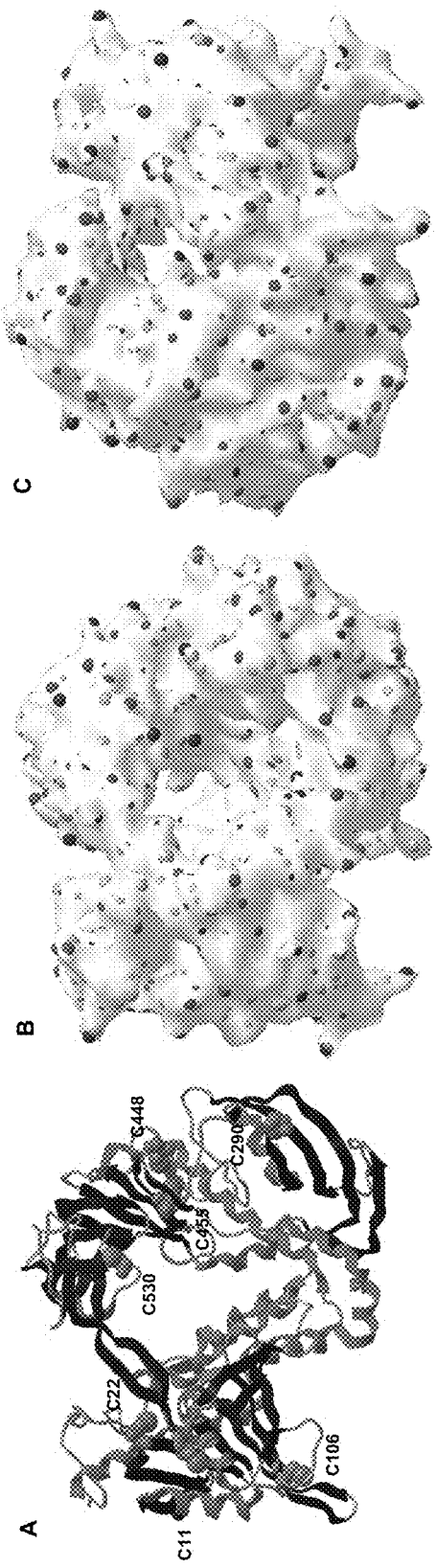
FIG. 9: Native cysteines and solvent accessible surface of phi-29 DNA polymerase (SEQ ID NO:4). (A) The seven native cysteines and their locations. (B) Front view of solvent accessible surface of phi-29 DNA polymerase. (C) Back view of solvent accessible surface of phi-29 DNA polymerase. The cysteine residues are shown in space filling model (A). The structures are generated using ChemBi03D Ultra 11.0 (CambridgeSoft).

We selected cysteine as the non-naturally occurring amino acid for the labeling sites on the surface. For post-translational labeling, we assessed the accessibility of the native cysteines to aqueous solvent. The solvent accessible surface of the polymerase is shown in FIG. 9; none of the 7 native cysteine residues are on the solvent accessible surface of phi-29 DNA polymerase. Thus the native cysteine residues will not be used as fluorescent labeling sites. These residues do no need to be replaced, because they are buried and not accessible for a labeling reaction.

Figure 10:
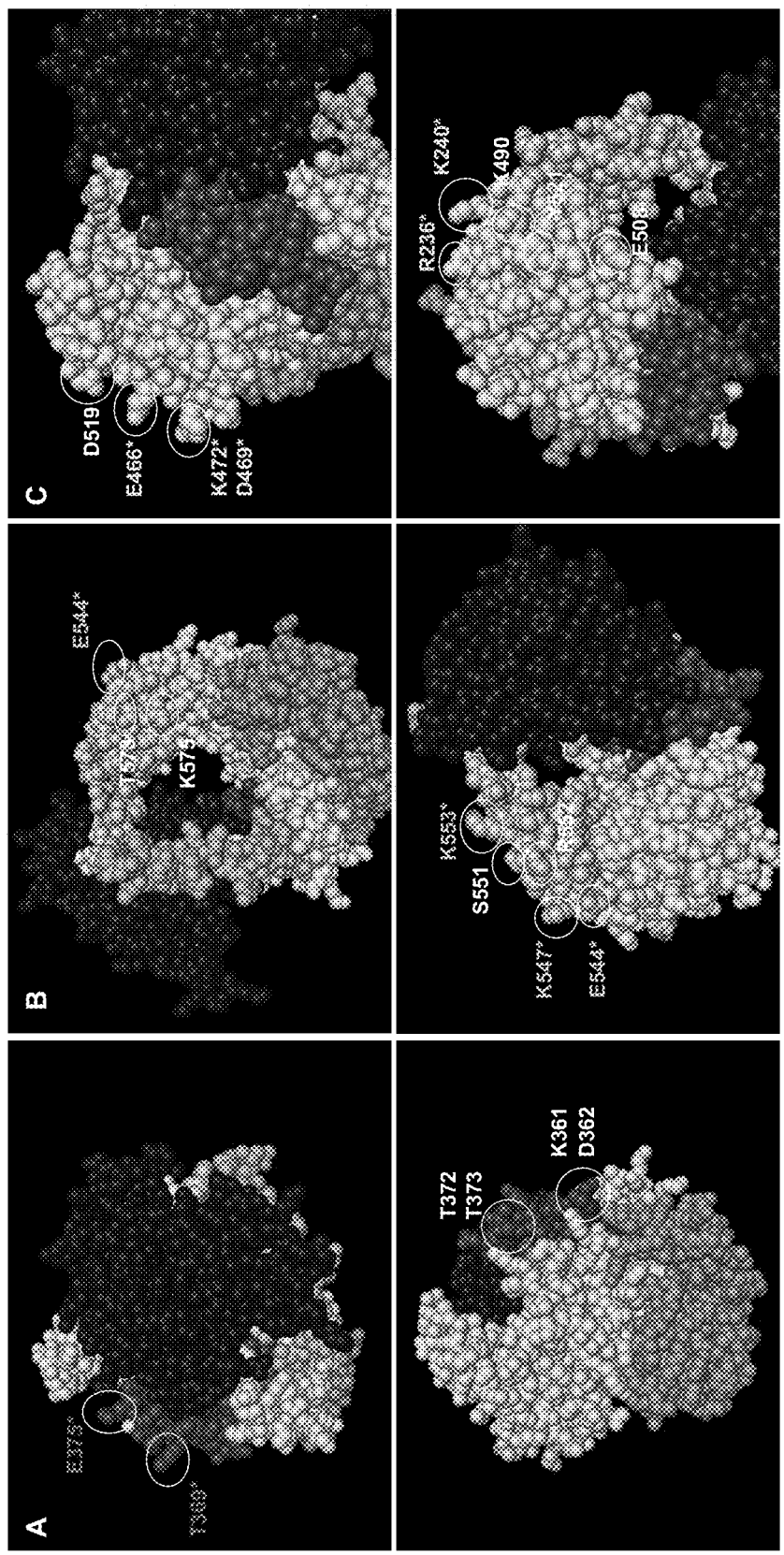
FIG. 10: Candidate residues for labeling on (A) finger, (B) thumb and (C) palm subdomains of phi-29 DNA polymerase (SEQ ID NO:4). The top and bottom panels displayed the front and back view, respectively. The proteins are shown in space-filled model. Candidate labeling sites are circled in white. The residues marked with a star represent labeling sites with preferred orientation. The structures are generated using PyMOL.
Figure 12:
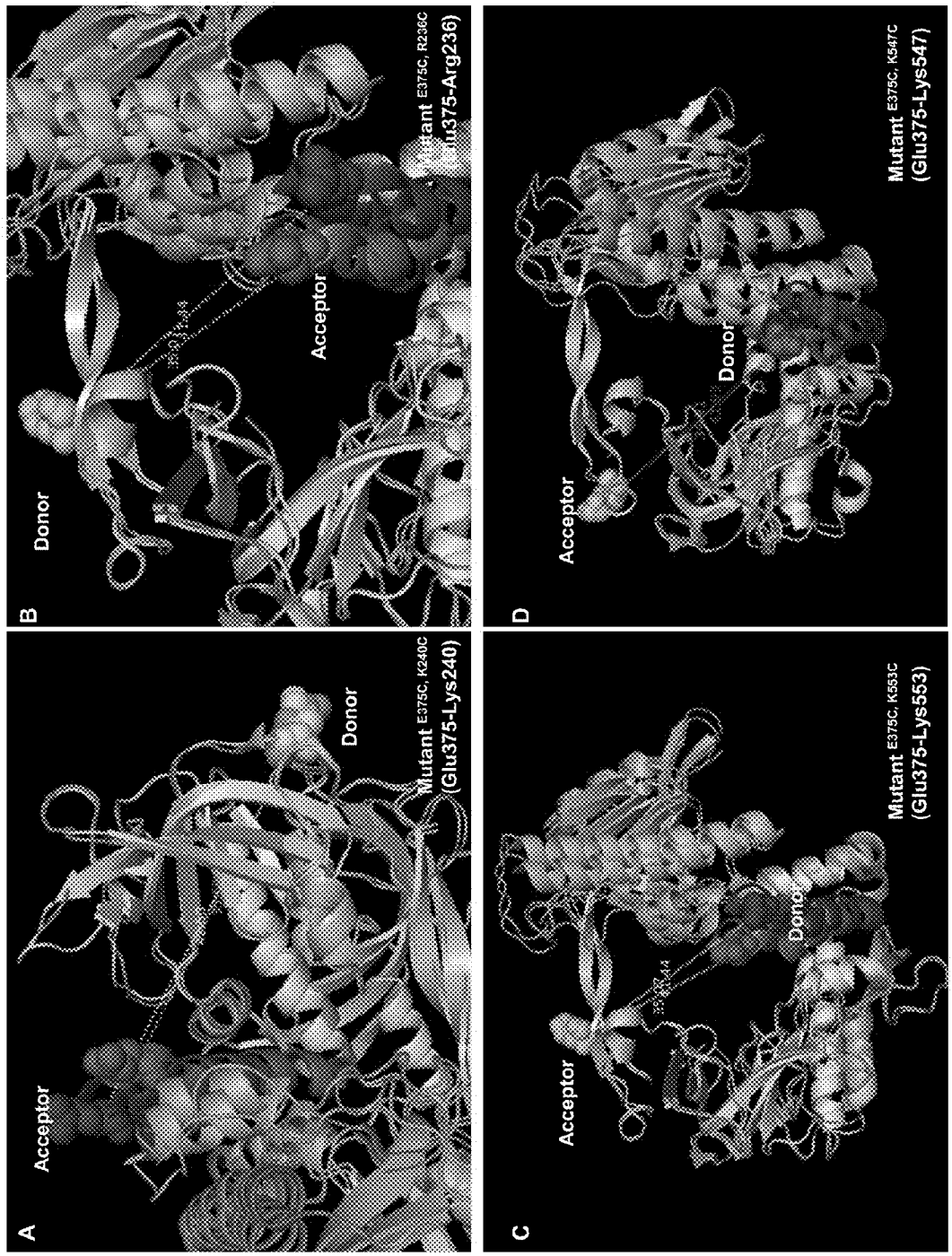
FIG. 12: Representatives of phi-29 DNA polymerase (SEQ ID NO:4) mutants to be constructed for labeling of FRET pairs. (A) Mutant$^{E375C, K240C}$, with labeling sites located on finger and palm subdomains, respectively; (B) Mutant$^{E375C, K553C}$ with labeling sites located on finger and thumb subdomains, respectively. (C) Mutant$^{E375C, K553C}$ with labeling sites located on finger and thump subdomains, respectively; (D) Mutant$^{E375C, K547C}$ with labeling sites located on finger and thumb subdomains, respectively. The open and closed form of proteins are shown in cartoon model and the labeling sites are shown in sphere model. Panels are generated using PyMOL.

Candidate residues to be used as FRET pairs on phi-29 DNA polymerase are shown in FIG. 10. The distances of those residue pairs are listed in Table 1, below. A FRET pair with larger change in distance before and after the binding of incoming nucleotide is preferred, as it will generate greater FRET signals. We have selected five pairs including Mutant$^{E375C, K240C}$, Mutant$^{E375C, R236C}$, Mutant$^{E375C, K553C}$, Mutant$^{E375C, K547C}$ and Mutant$^{E375C, E544C}$ with distance changes ($R_{open} - R_{closed}$) of 6.92 Å, 6.70 Å, 6.37 Å, 7.02 Å and 6.97 Å, respectively (FIG. 12). Those sites that are fully solvent accessible and have good orientation for simple and high-yield labeling are marked with a star in FIG. 10. To prevent significant structural perturbation and loss of polymerase activity, the key residues essential for structural and functional integrity of the polymerase are not included.

The change in distances between the candidate residues from the "open" to the "closed" form of phi-29 DNA polymerase (SEQ ID NO:4) are measured between $C_\alpha$ of the selected residues, and listed in Table 1.

TABLE 1

Target residues, distances between residues on finger and palm/thumb subdomains in both open and closed conformations, and change in distance (in Å)

| | | Distance and Distance Change (Å) | Finger Domain Residues | | | | | |
|---|---|---|---|---|---|---|---|---|
| | | | Tyr369 | Glu375 | Thr373 | Lys361 | Thr372 | Asp362 |
| Thumb Domain Residues | Lys553 | $d_{open}$ | 47.11 | 41.44 | 46.48 | 49.26 | 44.38 | 50.40 |
| | | $d_{closed}$ | 43.67 | 35.07 | 41.54 | 48.16 | 40.29 | 48.66 |
| | | $\Delta d$ | 3.44 | 6.37 | 4.94 | 1.10 | 4.09 | 1.74 |
| | Lys547 | $d_{open}$ | 45.14 | 41.93 | 45.22 | 45.84 | 42.21 | 48.04 |
| | | $d_{closed}$ | 41.73 | 34.91 | 40.00 | 45.24 | 37.76 | 46.80 |
| | | $\Delta d$ | 3.41 | 7.02 | 5.22 | 0.60 | 4.45 | 1.24 |
| | Glu544 | $d_{open}$ | 46.47 | 41.92 | 45.61 | 48.86 | 42.83 | 50.91 |
| | | $d_{closed}$ | 43.02 | 34.95 | 40.29 | 48.25 | 38.50 | 49.54 |
| | | $\Delta d$ | 3.45 | 6.97 | 5.32 | 0.61 | 4.33 | 1.37 |
| | Lys575 | $d_{open}$ | 46.22 | 43.93 | 47.10 | 45.40 | 44.11 | 47.52 |
| | | $d_{closed}$ | 42.69 | 36.92 | 41.92 | 44.44 | 39.52 | 46.02 |
| | | $\Delta d$ | 3.53 | 7.01 | 5.18 | 0.96 | 4.59 | 1.50 |
| | Arg552 | $d_{open}$ | 46.21 | 40.66 | 45.59 | 48.34 | 43.30 | 49.70 |
| | | $d_{closed}$ | 42.71 | 34.17 | 40.49 | 47.30 | 39.08 | 48.00 |
| | | $\Delta d$ | 3.50 | 6.49 | 5.10 | 1.04 | 4.22 | 1.70 |
| | Ser551 | $d_{open}$ | 46.89 | 42.26 | 46.62 | 48.29 | 44.08 | 49.92 |
| | | $d_{closed}$ | 43.36 | 35.48 | 41.47 | 47.27 | 39.74 | 48.27 |
| | | $\Delta d$ | 3.53 | 6.78 | 5.15 | 1.02 | 4.34 | 1.65 |
| | Thr573 | $d_{open}$ | 45.18 | 41.46 | 45.42 | 45.71 | 42.73 | 47.44 |
| | | $d_{closed}$ | 41.69 | 34.69 | 40.34 | 44.69 | 38.36 | 45.84 |
| | | $\Delta d$ | 3.49 | 6.77 | 5.08 | 1.02 | 4.37 | 1.60 |
| Palm Domain Residues | Glu466 | $d_{open}$ | 32.50 | 33.15 | 32.57 | 34.22 | 29.29 | 36.94 |
| | | $d_{closed}$ | 29.83 | 28.20 | 28.45 | 33.84 | 25.86 | 35.90 |
| | | $\Delta d$ | 2.67 | 4.95 | 4.12 | 0.38 | 3.43 | 1.04 |
| | Lys472 | $d_{open}$ | 26.57 | 30.64 | 28.08 | 26.31 | 24.63 | 29.31 |
| | | $d_{closed}$ | 23.58 | 25.68 | 23.79 | 25.82 | 20.79 | 28.13 |
| | | $\Delta d$ | 2.99 | 4.96 | 4.29 | 0.49 | 3.84 | 1.18 |
| | Asp469 | $d_{open}$ | 31.43 | 35.25 | 32.97 | 30.48 | 29.49 | 33.67 |
| | | $d_{closed}$ | 27.90 | 29.95 | 28.39 | 28.87 | 25.24 | 31.55 |
| | | $\Delta d$ | 3.53 | 5.30 | 4.58 | 1.61 | 4.25 | 2.12 |
| | Lys240 | $d_{open}$ | 44.19 | 42.60 | 44.61 | 44.25 | 41.25 | 46.96 |
| | | $d_{closed}$ | 40.70 | 35.68 | 39.32 | 43.53 | 36.62 | 45.65 |
| | | $\Delta d$ | 3.49 | 6.92 | 5.29 | 0.72 | 4.63 | 1.31 |
| | Arg236 | $d_{open}$ | 43.50 | 44.15 | 44.97 | 41.49 | 41.32 | 44.63 |
| | | $d_{closed}$ | 40.05 | 37.45 | 39.84 | 40.72 | 36.62 | 43.38 |
| | | $\Delta d$ | 3.45 | 6.70 | 5.13 | 0.77 | 4.70 | 1.25 |

TABLE 1-continued

Target residues, distances between residues on finger and palm/thumb subdomains in both open and closed conformations, and change in distance (in Å)

| | Distance and Distance Change (Å) | Finger Domain Residues | | | | | |
|---|---|---|---|---|---|---|---|
| | | Tyr369 | Glu375 | Thr373 | Lys361 | Thr372 | Asp362 |
| Asp519 | $d_{open}$ | 35.11 | 32.05 | 33.11 | 40.24 | 30.67 | 42.15 |
| | $d_{closed}$ | 33.04 | 27.65 | 29.41 | 40.58 | 28.22 | 41.65 |
| | Δd | 2.07 | 4.40 | 3.70 | −0.34 | 2.45 | 0.50 |
| Glu508 | $d_{open}$ | 30.15 | 23.02 | 26.45 | 38.19 | 25.03 | 39.02 |
| | $d_{closed}$ | 27.67 | 18.58 | 22.41 | 37.88 | 22.68 | 37.77 |
| | Δd | 2.48 | 4.44 | 4.04 | 0.31 | 2.35 | 1.25 |
| Tyr521 | $d_{open}$ | 33.71 | 28.78 | 31.14 | 39.81 | 28.94 | 41.36 |
| | $d_{closed}$ | 30.91 | 23.58 | 26.58 | 39.57 | 25.85 | 40.20 |
| | Δd | 2.80 | 5.20 | 4.56 | 0.24 | 3.09 | 1.16 |
| Lys490 | $d_{open}$ | 36.94 | 33.72 | 35.86 | 40.26 | 32.92 | 42.46 |
| | $d_{closed}$ | 33.74 | 27.38 | 30.81 | 39.83 | 28.90 | 41.25 |
| | Δd | 3.20 | 6.34 | 5.05 | 0.43 | 4.02 | 1.21 |

Thus, within a single polymerase, there are many candidate residues that can be used for FRET pair(s) labeling. Significant change in distance (a few Å or more) occurs when the polymerase transits from the "open" to the "closed" conformation, which will result in large observable FRET signals. Those expected to result in the largest observable FRET signals are highlighted in bold in Table 1. These target sites can be used to monitor the chemo-mechanical process of DNA synthesis, to further characterize the FRET signature associated with each one of the four different base types, and to identify chemically modified bases (such as methyl-C) for real-time DNA and epigenetic sequencing.

Example 2

In Vitro Translation of a Labeled DNA Polymerase

Figure 6:
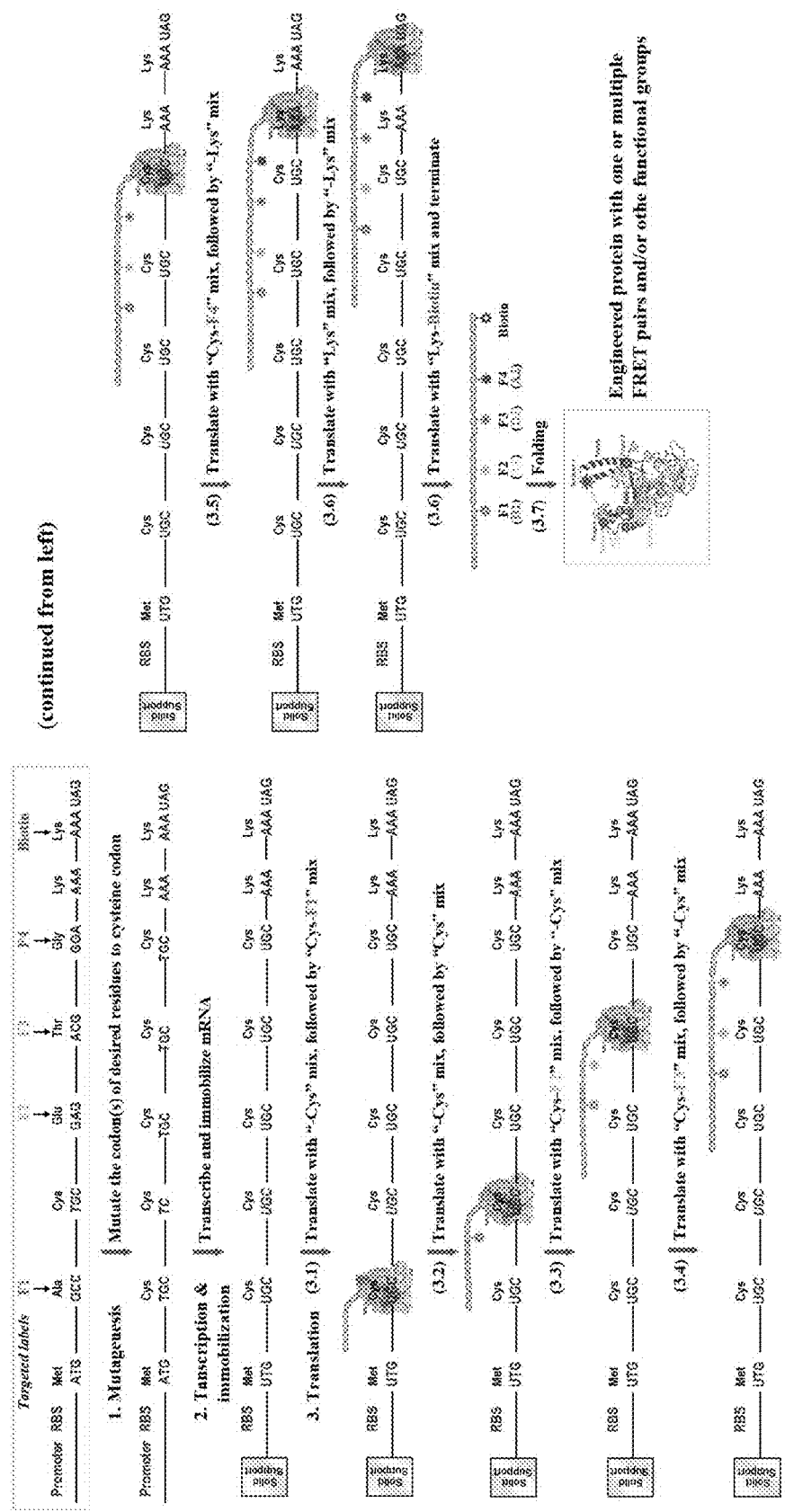
FIG. 6. Method for incorporating multiple FRET pairs into polymerase by automated cyclic in vitro translation on solid supports.

We have designed an efficient method for engineering labeled DNA polymerases with multiple labels positioned at designated residues. The general concept is illustrated in FIG. 6. For simplicity, the solid lines separating each named amino acid represent additional amino acids that are not shown.

The DNA polymerase coding sequence is cloned into a vector. The vector also includes regulatory sequences necessary for transcription (e.g. T7 promoter), translation initiation (ribosomal binding site—RBS, and start codon—ATG), and termination (stop codon –UAG). The codons encoding the targeted residues for labeling are mutated to a codon encoding a cysteine residue (TGC) using standard molecular biology methods.

The mRNA molecules are captured on a solid support by hybridization of a sequence at one end of the RNA molecules to a complementary oligonucleotide or PNA (peptide nucleic acid) immobilized on the solid support. The mRNA molecule could also be immobilized using biotin. The solid support (e.g., solid polysterene or silica beads) are packed into a column. The cyclic synthesis is automated by using a computer-controlled liquid handling system which consists of a multi-port motorized valve and syringe pumps to deliver reagents and to perform washing. Pneumatic system consisting of a vacuum or pressure source and motorized multiport valve system can also be used. Automated synthesis can also performed in batch mode with solid supports suspended in reagents or wash solution in a vessel. The supports can be captured by magnetic field or gravity.

A well-defined in vitro translation system will be used for the in vitro translation of the genetically engineered mRNA molecules into protein molecules with label(s) at the desired residue(s). A commercially available in vitro translation system (available from Roche, New England Biolabs or Promega Corporation) will be customized into 3 translation mixtures:

"-Cys" mix: complete in vitro translation mix lacking cysteine, but containing all other 19 amino acids;

"Cys" mix: complete in vitro translation mix containing only cysteine, and none of the other amino acids; and "Cys-X" mix: complete in vitro translation mix containing only X-labeled cystein and none of the other amino acids. X=the desired label, such as fluorescien or biotin.

The complete in vitro translation mix contains ingredients for in vitro translation including the ribosomes, aminoacyl tRNA synthetases for all the amino acids, ATP, GTP, and translation initiation, elongation and termination factors. The translation of the whole protein will be performed on solid support in cycles, each containing one of the 3 different mixtures. Translation starts from the start codon from the amino terminus and terminates at the carboxyl terminus.

First, the –Cys mix is added, to allow translation of the nascent protein up to the first Cys residue. Then, depending on whether a natural Cys, or a labeled Cys, is desired at the first Cys residue, the appropriate mix is added. No further residues will be added because the next codon will not encode for Cys. The cycles are repeated, with the appropriate Cys mix added at each residue, until the entire polymerase is translated.

If necessary, the labeled polypeptides are folded into functional proteins and purified by chromatography or affinity capture (e.g. biotin-avidin capture). The identity and purity of the products can be determined by mass spectrometry and SDS-PAGE gel electrophoresis.

We selected cysteine as the labeling site because it is easily labeled with an organic fluorescent dye molecule, e.g., using the specific reaction between the sulfhydryl group on the cysteine and the maleimide labeled on the dye molecule. Other residues with a functional group, such as lysine, can be used as well. Labeled cysteine charged to its cognate tRNA molecule can be efficiently incorporated into the growing peptide chain by the ribosome both in vivo and in vitro (Chin et al. (2003) *Science* 301:964; Xie & Schultz (2005) *Methods* 36:227-38; Kobs et al. (2001) *Nat. Biotechnol.* 21:1093-97; and Traverso et al. (2003) *J Biol. Chem.* 291:8509-12). The ribosome remains bound on the mRNA when the translation is stalled. In case the aminoacyl tRNA synthetase is not capable of activating the cysteine-tRNA with the corresponding labeled amino acid, the labeling can be performed after charging the tRNA with the un-labeled amino acid. A DNA polymerase can be labeled according to the present method with any combination of the desired fluorescent dyes at multiple positions. If necessary, the polymerase can be refolded after translation into an active functional molecule, using chromatography to purify after refolding.

Example 3

READS Technology Using Immobilized DNA Polymerase

DNA polymerases are labeled as described above, and immobilized on glass coverslips. The surface of a glass coverslip is derivatized with a streptavidin. The glass coverslip is first cleaned with the RCA protocol, derivatized with amine group with aminoalkyl (e.g. gamma-aminopropyl) triethoxysilane, and then functionalized with biotin with NHS ester-PEG-biotin (e.g. NHS ester-PEG 5000-Biotin). The biotinylated surface can be patterned into highly-ordered arrays with feature size and spacing optimal for assembly of single molecular arrays and fluorescent imaging efficiency.

The biotinylated coverslip is then assembled into a flowcell for further functionalization with streptavidin. The biotinylated surface is functionalized with streptavidin by incubating the glass coverslip with a streptavidin solution, e.g. 1 μM streptavidin in a buffer solution such as phosphate buffer saline (PBS, 137 mM NaCl, 2.7 mM KCl, 10 mM sodium phosphate dibasic, 2 mM potassium phosphate monobasic) plus 0.1% Tween 20.

The flowcell comprises of the glass coverslip substrate assembled on a glass slide or a stainless steel plate via a silicone rubber gasket with pre-patterned channels for the reaction. There are holes drilled out in the glass slide or stainless steel plate for fluidic port connection. A streptavidin solution (e.g. 1 μM streptavidin in PBS plus 0.1% Tween 20) is flowed into the flow cell to saturate the biotinylated surface with streptavidin, followed by a wash with buffer solution (e.g. PBS plus 0.1% Tween 20). The flowcell is assembled into an apparatus with precise temperature control and microfluidics, and a window for efficient fluorescence imaging.

A solution of the labeled polymerases in a proper buffer (e.g. PBS plus 0.1% Tween 20 and 1% BSA) is then flowed into the flowcell. The immobilization is monitored in real time with TIRF to ensure the proper density of the polymerase on the surface. We want them to be evenly distributed and well separated to pack maximum density of polymerases which still can be optically resolved by the imaging optics, e.g., on average 200 nm or more apart using a 100×/1.45NA oil objective and an EMCCD with 8 μm×8 μm pixels, or on average 400 nm or more apart using a 20×/1.2NA water immersion objective. Once the optimal density of polymerases has been achieved, the remaining polymerases are washed away with the wash buffer. To prevent protein denaturation, the flowcell is kept with a buffer solution in the flow channels at all time.

The DNA polymerases can also be immobilized by covalent attachment using a glass coverslip functionalized with a chemical group reactive toward amine (e.g. NHS ester) or reactive toward carboxylate (e.g. amine). Similar procedure is used for the immobilization.

Template DNA is prepared for sequencing by READS by ligating an adaptor oligonucleotide with a primer pre-hybridized on one strand of the adaptor. The 3'-OH of the primer will serve as the priming site for DNA synthesis. Exemplary template DNA is fragmented genomic DNA. If the labeled DNA polymerase has strong strand-displacement activity (such as phi-29), double-stranded or single-stranded DNA can be used. If the labeled DNA polymerase does not, however, have strong strand-displacement, a single-stranded template should be used.

A gap will be provided between the primer 3' OH group and the 5' end of the template DNA to ensure proper initial DNA synthesis from the priming site. This is because phi-29 cannot initiate strand-displacement DNA synthesis from a nick. The length of the adaptor sequence and primer should be such that efficient ligation can be performed and the primer remains hybridized under the condition for sequencing. The adaptor sequence contains a recognition site for a nicking endonuclease (e.g., Nt.BspQI) and the primer site is provided by nicking one strand of ligated template with a nicking enzyme. The adaptor sequence (e.g. polyA) is added to the 3' end of the DNA template by a terminal transferase and the primer is hybridized onto the added adaptor sequence (e.g., with a polyT sequence).

The template DNA molecules are then loaded onto the polymerases. More specifically, the primed DNA template in a buffer solution (e.g. 50 mM TrisCl, 100 mM NaCl, 0.1% Triton X-100, 1% bovine serum albumin (BSA), pH 7.0) is flowed into the flowcell where the DNA polymerases have been immobilized on the surface of the glass coverslip.

The adaptor sequence or the primer also contains a fluorescent label so that the loading of the DNA template can be monitored in real time. Once the most or all DNA polymerases have been loaded with a primed template, the rest of the DNA templates are removed by a single wash with a buffer (e.g. 20 mM TrisCl, 100 mM NaCl, 0.1% Triton X-100, pH7.0). To reduce exonuclease activity, the $Mg^{2+}$ or other ion essential for polymerase activity can be removed or chelated by the addition of 10-20 mM of EDTA in the loading and wash buffer. For single stranded DNA template, high concentration (e.g. 4 μM) of single-stranded DNA binding protein (SSB, e.g. from *E. coli*) is included in the loading buffer to prevent non-specific binding of the single stranded DNA onto the DNA polymerases (which may have a high binding affinity to single-stranded DNA). For DNA polymerases which require SSB for efficient strand displacement activity (e.g. Klenow and Sequenase version 2.0), high concentration (e.g. 4 μM) of SSB is added into the reaction solution.

Synthesis is initiated by the addition of dNTP's in a buffer solution into the flowcell. For phi-29, the reaction mix can be: 1 to 100 μM of each of the dNTPs (dATP, dCTP, dGTP and dTTP) in 20 mM TrisCl, 10 mM $(NH4)_2SO_4$, 4 mM $MgSO_4$, 0.1% Triton X-100, 100 μg/ml BSA and 4 μM SSB, pH8.8.

The temperature of the flowcell is set to the desired point or range with a built-in temperature control device such as a thermal electric module. The rate of the polymerization reaction can controlled, to some degree, by performing the reaction at the desired temperature (e.g. ~5 bases/s at 4° C., ~25 bases/s at 16° C., and ~40 bases/s at 30° C. for phi-29 DNA polymerase under a condition where the dNTP concentration is above the $K_M$ of the nucleotide). The sequencing reaction is ideally performed with dNTP concentration near or a few fold above the $K_M$ of the dNTP. The concentration of each of the dNTP can be different, but the concentration of each dNTP should result in approximately the same incorporation rate for each. The reaction rate can also be controlled by using a lower concentration of nucleotides.

Phi-29 DNA polymerase has a very strong proofreading function (3' to 5' exonuclease activity). To prevent the removal of the primer in the absence of dNTP's, oligonucleotides with thiophosphate linkages, PNAs, or other exonuclease resistant nucleotides can be used. Phi-29 also has a very strong strand displacement capability, meaning the DNA template need not be single-stranded. Alternatively, $Mg^{2+}$ is removed from the polymerases by adding 10-20 mM of a chelator (e.g. EDTA) into the buffer used for loading the DNA template. As illustrated in Example 1, a genetically engineered exonuclease-deficient phi-29 DNA polymerase can be used.

Preparation of genomic DNA for READS is straightforward. The genomic DNA molecules are randomly fragmented into the desired size by hydrodynamic shearing (Joneja & Huang (2009) *Biotechniques* 46:553-56). We have developed an inexpensive instrument for hydrodynamic shearing of genomic DNA. The sheared genomic DNA fragments are end-repaired using standard molecular biology techniques. The primed adaptor is then ligated to the DNA fragments. After excess adaptor is removed by size-selection centrifugation, the genomic DNA is ready for sequencing. Alternatively, a homopolymer polynucleotide (such as polyA with ~50 A's) adaptor can be added to the 3' ends of the genomic DNA fragments using a terminal transferase, and then hybridized to a primer with a polyT 50mer.

Use of an immobilized DNA polymerase can limit the read length, due to the limited photostability of any given FRET dye. With a more elaborate network of FRET pairs and more sophisticated excitation patterns, however, we can (1) increase the informational content of the FRET traces with redundancy for more accurate reads; and (2) use the FRET dyes in serial detections to extend their lifetime, thereby increasing read lengths. Photobleaching can be minimized by the addition of enzymatic oxygen scavenger system (e.g. 100 nM glucose oxidase, 1.5 µM catalase, 56 mM glucose) into the reaction solution or thorough removal of oxygen in the reaction solution by bubbling with water-saturated argon.

Dye blinking can also be an issue in single-molecule imaging, but can be minimized using known techniques (e.g. addition of a triplet quencher such as Trolox in the reaction solution). Addition of additional FRET pairs in parallel will also compensate for any missing information if one dye blinks.

One of skill will recognize that similar techniques can be applied using labeled RNA polymerases. The RNA polymerases can be immobilized using the same procedures for immobilizing the DNA polymerase as described above. The adaptor sequence to be added to the DNA template contains a promoter sequence for the RNA polymerase. A primer is not needed for RNA polymerization. The nucleotide substrates for synthesis are ribonucleotide tripphosphates (rNTPs) instead of dNTPs. The sequencing reaction is performed using the procedures similar to sequencing with DNA polymerase.

Similarly, the labeled polymerase can be reverse transcriptase. The reverse transcriptase can be immobilized using the same procedures for immobilizing the DNA polymerase. The RNA template for sequencing is prepared using the same procedures as described for DNA sequencing with labeled DNA polymerases. The nucleotide substrates for synthesis are also the same deoxyribonucleotide tripphosphates (dNTPs). In some embodiments, the templates to be sequence are single-stranded RNA molecules, e.g., mRNA molecules. Where the mRNA molecules are from eukaryotes, they will already contain a polyA tail at the 3' ends, and poly T can be used as the primer (e.g., a polyT 50mer). For other RNA, a DNA or RNA adaptor can be ligated to the RNA molecule and hybridized with a primer for sequencing. The sequencing reaction is performed using the procedures similar to sequencing with DNA polymerase.

Example 4

READS Technology Using Immobilized DNA Template

Another variant of READS technology is to immobilize the template DNA molecules, and to read along the templates one stretch at a time by repeated loading of the DNA polymerase. This approach is beneficial since the photostability of the FRET labels on a single DNA polymerase is limited, i.e., they will become photobleached over time with continuous imaging. If the DNA is immobilized, a labeled polymerase can be allowed to read a certain length of sequence, quickly removed, and another labeled polymerase loaded to read the next stretch of sequence.

In this case, the total read length is limited by the penetration depth used in TIRF imaging if the DNA is attached at only one end. Longer DNA molecules extending from a surface too far above the penetration depth of the TIRF evanescent wave excitation cannot be reliably imaged. One way to alleviate this problem is to stretch the DNA onto the surface and capture both ends so that the long DNA molecule remains in the TIRF illumination range at all times. This is illustrated in FIG. 14.

To attach both ends to the surface, the template DNA has a biotin label at one end and a "caged biotin" at the other end. The term "caged" refers to a biotin physically enclosed by or chemically protected by a chemical moiety (e.g. methyl α-nitropiperonyloxycarbonyl biotin) which can be uncaged chemically or photochemically. The term "uncaged" refers to chemically or photochemically unprotecting the biotin moiety so that it is available for binding to avidin or streptavidin.

The labeled DNA template is loaded into the flowcell with the glass coverslip derivatized with streptavidin as described earlier. After the biotinylated end of the DNA is immobilized, the DNA molecule is stretched by hydrodynamic shear flow. The "caged biotin" moiety is uncaged by illumination with the light of appropriate wavelength (320-380 nm for uncaging methyl α-nitropiperonyloxycarbonyl biotin) while the DNA is still stretched by the continuous hydrodynamic shear flow, thereby allowing the now uncaged biotin to bind to the streptavidin on the surface.

Figure 14:
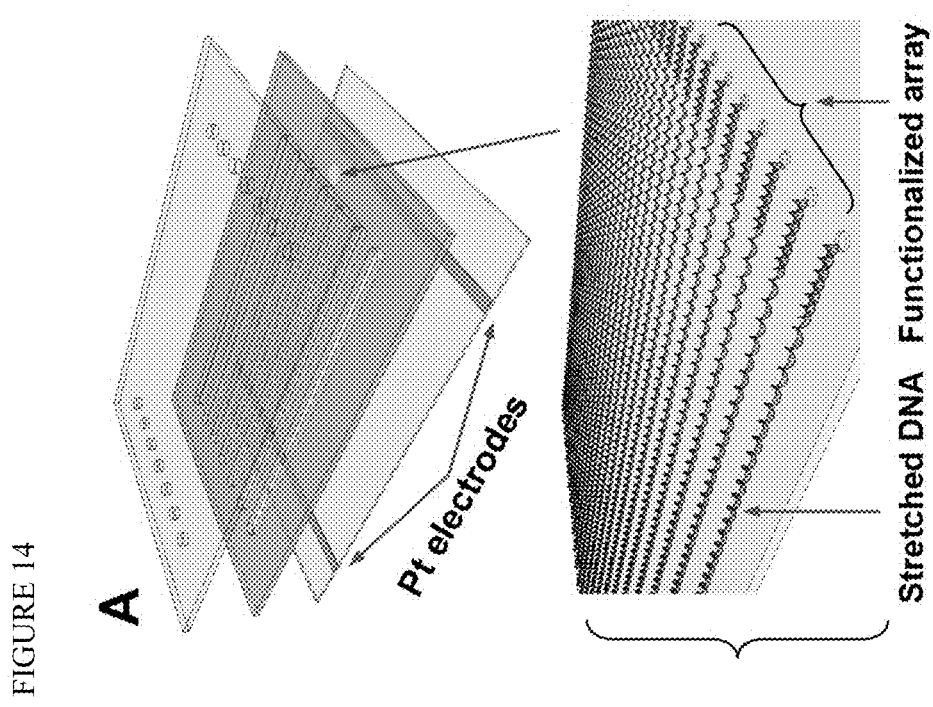
FIG. 14: Microfabricated device for anchoring and stretching of long DNA molecules. (A) Overall design. (B) Full EMCCD fluorescence image of end-captured DNA molecules stretched with 320 V/cm electric field.

Alternatively, after the biotinylated end of the DNA is immobilized the DNA molecule can be electrophoretically stretched by applying an electric field or voltage (e.g. 160 V/cm) across or along the flow cell using built-in or external electrodes, and then the "caged biotin" moiety is uncaged by illumination with the light of appropriate wavelength (320-380 nm for uncaging methyl α-nitropiperonyloxycarbonyl biotin) while the DNA is still stretched by the electric field, thereby allowing the now uncaged biotin to bind to the streptavidin on the surface (FIG. 14). A buffer with low conductance (e.g. 0.05×TBE, 4.5 mM Tris borate, 0.1 mM EDTA, pH 8.0) is used for optimal stretching while minimizing joule heating.

Generally, each end of the template is attached to the surface, and not intervening sequence. This is to avoid interference with the DNA synthesis. PEG (e.g., PEG5000) can be coated on to the surface of the substrate to minimize the non-specific binding of DNA molecules.

The primer for sequencing is typically hybridized after the molecules have been stretched and immobilized at both ends.

Once the template DNA is attached to the substrate, a first labeled DNA polymerase is loaded as described in Example 3. The DNA synthesis reaction is started by flowing in the reaction mix containing dNTPs in the reaction buffer, e.g. 1 to 100 µM of each of the dNTPs (dATP, dCTP, dGTP and dTTP)

in a reaction buffer (20 mM TrisCl, 10 mM (NH4)$_2$SO$_4$, 4 mM MgSO$_4$, 0.1% Triton X-100, 100 µg/ml BSA and 4 µM SSB, pH8.8) for phi-29 DNA polymerase. If T7 DNA polymerase or Sequenase version 2.0 is used, the reaction mix will include 1 to 100 µM of each of the dNTPs in a reaction buffer (20 mM TrisCl, 10 mM MgCl$_2$, 50 mM NaCl, 10 mM DTT, 0.1% Triton X-100, 100 µg/ml BSA and 4 µM SSB, pH8.0).

A number of images will be taken that falls well within the lifetime of the FRET dyes used on the polymerase (e.g., less than 100,000 measurements using Alexa dyes, as explained above). Once this number is reached, the reaction is halted by washing away the dNTPs and polymerase, e.g., by a rapid introduction of a wash solution containing 50 mM TrisCl, 20 mM EDTA, 100 mM NaCl, and sodium dodecyl sulfate (SDS), pH 8.0 at 60° C. into and through the flowcell. The concentration of the SDS is such that the solution partially denatures the DNA polymerase but does not weaken the biotin-streptavidin binding enough to result in loss of the DNA template. Dual or multiple biotin labels on each end of the DNA template can be used to reduce the risk of loss of the DNA template during this wash step. Once the polymerase is removed from the DNA template, the flowcell is then washed again with the appropriate reaction buffer (e.g., 50 mM TrisCl, 20 mM EDTA, 100 mM NaCl, 0.1% Triton X-100, pH 8.0).

The next labeled DNA polymerase is loaded onto the primed DNA template by flowing a new solution of labeled DNA polymerase into the flowcell as described above, followed by the reaction mix. The polymerase continues where the previous one left off, using the 3' end of the nascent strand as a "primer." This process is repeated until the end of the DNA strand is reached.

If a double stranded DNA template is used, a second primer can be hybridized to the opposite end of the template so that the sequencing reaction is performed on both strands of the double stranded DNA molecule. The redundant information provides more accurate sequencing of the DNA molecule. In addition, new primers can be hybridized to slightly offset positions on the DNA template so that another round of sequencing is performed. This process can be repeated to achieve the ultimate sequencing accuracy if desired.

This process potentially allows for very long read lengths. Sequences up to several hundred thousand bases (e.g., 200,000 bases) can be stretched on a substrate. However, the density of the DNA molecules must be such that there is minimal overlap. The entirety of the long sequence is maintained close to the surface within the penetration depth of the TIRF as described. Many DNA templates are sequenced in parallel using the flowcell and wide-field single molecule FRET imaging, with area sensors such as EMCCD cameras.

What is claimed is:

1. A labeled DNA polymerase, wherein said DNA polymerase comprises at least one FRET donor and at least one FRET acceptor, wherein said FRET donor and FRET acceptor are positioned on the DNA polymerase so that when the polymerase adds a nucleotide to the nascent strand of DNA, a distinct FRET signal is generated at least depending on which base (A, C, G, T) is incorporated, wherein:

the FRET acceptor is positioned on the finger domain of the DNA polymerase and the FRET donor is positioned on the thumb domain of the DNA polymerase; or wherein the FRET donor is positioned on the finger domain of the DNA polymerase and the FRET acceptor is positioned on the thumb domain of the DNA polymerase, the labeled DNA polymerase is a phi-29 DNA polymerase, and wherein the phi-29 DNA polymerase comprises E375C and K240C mutations.

2. The labeled DNA polymerase of claim 1, wherein the FRET donor is within 10 angstroms of the Förster radius ($R_o$) from the FRET acceptor when the DNA polymerase is in the open position.

3. The labeled DNA polymerase of claim 1, wherein the Förster radius between the FRET donor and the FRET acceptor changes at least 2.5 angstroms from the open position to the closed position of the DNA polymerase.

4. The labeled DNA polymerase of claim 1, further comprising at least a second FRET donor and at least a second FRET acceptor.

5. The labeled DNA polymerase of claim 1, wherein the FRET donor and FRET acceptor are positioned so that a distinct FRET signal is generated when the DNA polymerase reads a methylated nucleotide on the template DNA.

6. A system for real time sequencing of a DNA molecule comprising the labeled DNA polymerase of claim 1 and optical instrumentation capable of detecting a FRET signal from a single molecule.

7. The labeled DNA polymerase of claim 1, wherein the FRET donor and the FRET acceptor are separately linked to different amino acid residues selected from:

E375C and K240C.

8. The labeled DNA polymerase of claim 1, wherein the labeled DNA polymerase is labeled with more than one FRET pair, wherein the FRET donor in each FRET pair is within 10 angstroms of the Förster radius ($R_o$) from the FRET acceptor in each FRET pair when the DNA polymerase is in the open position.

9. The labeled DNA polymerase of claim 1, wherein the FRET acceptor is positioned on the finger domain of the DNA polymerase and the FRET donor is positioned on the thumb domain of the DNA polymerase.

10. The labeled DNA polymerase of claim 1, wherein the FRET acceptor is positioned on the thumb domain of the DNA polymerase and the FRET donor is positioned on the finger domain of the DNA polymerase.

11. The system of claim 6, comprising a plurality of DNA molecules immobilized onto a substrate.

12. The system of claim 11, wherein the DNA molecules are attached to the substrate at more than one site.

13. The labeled DNA polymerase of claim 1, wherein the Förster radius between the FRET donor and the FRET acceptor changes 1-10 angstroms from the open position to the closed position of the DNA polymerase.

* * * * *

SEQUENCE LISTING

```
<160> NUMBER OF SEQ ID NOS: 6

<210> SEQ ID NO 1
<211> LENGTH: 903
<212> TYPE: PRT
<213> ORGANISM: Enterobacteria phage rb69

<400> SEQUENCE: 1

Met Lys Glu Phe Tyr Leu Thr Val Glu Gln Ile Gly Asp Ser Ile Phe
1               5                   10                  15

Glu Arg Tyr Ile Asp Ser Asn Gly Arg Glu Arg Thr Arg Glu Val Glu
            20                  25                  30

Tyr Lys Pro Ser Leu Phe Ala His Cys Pro Glu Ser Gln Ala Thr Lys
        35                  40                  45

Tyr Phe Asp Ile Tyr Gly Lys Pro Cys Thr Arg Lys Leu Phe Ala Asn
    50                  55                  60

Met Arg Asp Ala Ser Gln Trp Ile Lys Arg Met Glu Asp Ile Gly Leu
65                  70                  75                  80

Glu Ala Leu Gly Met Asp Asp Phe Lys Leu Ala Tyr Leu Ser Asp Thr
                85                  90                  95

Tyr Asn Tyr Glu Ile Lys Tyr Asp His Thr Lys Ile Arg Val Ala Asn
            100                 105                 110

Phe Asp Ile Glu Val Thr Ser Pro Asp Gly Phe Pro Glu Pro Ser Gln
        115                 120                 125

Ala Lys His Pro Ile Asp Ala Ile Thr His Tyr Asp Ser Ile Asp Asp
    130                 135                 140

Arg Phe Tyr Val Phe Asp Leu Leu Asn Ser Pro Tyr Gly Asn Val Glu
145                 150                 155                 160

Glu Trp Ser Ile Glu Ile Ala Ala Lys Leu Gln Glu Gln Gly Gly Asp
                165                 170                 175

Glu Val Pro Ser Glu Ile Ile Asp Lys Ile Ile Tyr Met Pro Phe Asp
            180                 185                 190

Asn Glu Lys Glu Leu Leu Met Glu Tyr Leu Asn Phe Trp Gln Gln Lys
```

-continued

```
            195                 200                 205
Thr Pro Val Ile Leu Thr Gly Trp Asn Val Glu Ser Phe Ala Ile Pro
210                 215                 220

Tyr Val Tyr Asn Arg Ile Lys Asn Ile Phe Gly Glu Ser Thr Ala Lys
225                 230                 235                 240

Arg Leu Ser Pro His Arg Lys Thr Arg Val Lys Val Ile Glu Asn Met
                245                 250                 255

Tyr Gly Ser Arg Glu Ile Ile Thr Leu Phe Gly Ile Ser Val Leu Asp
                260                 265                 270

Tyr Ile Asp Leu Tyr Lys Lys Phe Ser Phe Thr Asn Gln Pro Ser Tyr
            275                 280                 285

Ser Leu Asp Tyr Ile Ser Glu Phe Glu Leu Asn Val Gly Lys Leu Lys
290                 295                 300

Tyr Asp Gly Pro Ile Ser Lys Leu Arg Glu Ser Asn His Gln Arg Tyr
305                 310                 315                 320

Ile Ser Tyr Asn Ile Ile Ala Val Tyr Arg Val Leu Gln Ile Asp Ala
                325                 330                 335

Lys Arg Gln Phe Ile Asn Leu Ser Leu Asp Met Gly Tyr Tyr Ala Lys
                340                 345                 350

Ile Gln Ile Gln Ser Val Phe Ser Pro Ile Lys Thr Trp Asp Ala Ile
            355                 360                 365

Ile Phe Asn Ser Leu Lys Glu Gln Asn Lys Val Ile Pro Gln Gly Arg
370                 375                 380

Ser His Pro Val Gln Pro Tyr Pro Gly Ala Phe Val Lys Glu Pro Ile
385                 390                 395                 400

Pro Asn Arg Tyr Lys Tyr Val Met Ser Phe Asp Leu Thr Ser Leu Tyr
                405                 410                 415

Pro Ser Ile Ile Arg Gln Val Asn Ile Ser Pro Glu Thr Ile Ala Gly
                420                 425                 430

Thr Phe Lys Val Ala Pro Leu His Asp Tyr Ile Asn Ala Val Ala Glu
            435                 440                 445

Arg Pro Ser Asp Val Tyr Ser Cys Ser Pro Asn Gly Met Met Tyr Tyr
450                 455                 460

Lys Asp Arg Asp Gly Val Val Pro Thr Glu Ile Thr Lys Val Phe Asn
465                 470                 475                 480

Gln Arg Lys Glu His Lys Gly Tyr Met Leu Ala Ala Gln Arg Asn Gly
                485                 490                 495

Glu Ile Ile Lys Glu Ala Leu His Asn Pro Asn Leu Ser Val Asp Glu
                500                 505                 510

Pro Leu Asp Val Asp Tyr Arg Phe Asp Phe Ser Asp Glu Ile Lys Glu
            515                 520                 525

Lys Ile Lys Lys Leu Ser Ala Lys Ser Leu Asn Glu Met Leu Phe Arg
530                 535                 540

Ala Gln Arg Thr Glu Val Ala Gly Met Thr Ala Gln Ile Asn Arg Lys
545                 550                 555                 560

Leu Leu Ile Asn Ser Leu Tyr Gly Ala Leu Gly Asn Val Trp Phe Arg
                565                 570                 575

Tyr Tyr Asp Leu Arg Asn Ala Thr Ala Ile Thr Thr Phe Gly Gln Met
                580                 585                 590

Ala Leu Gln Trp Ile Glu Arg Lys Val Asn Glu Tyr Leu Asn Glu Val
            595                 600                 605

Cys Gly Thr Glu Gly Glu Ala Phe Val Leu Tyr Gly Asp Thr Asp Ser
610                 615                 620
```

```
Ile Tyr Val Ser Ala Asp Lys Ile Asp Lys Val Gly Glu Ser Lys
625                 630                 635                 640

Phe Arg Asp Thr Asn His Trp Val Asp Phe Leu Asp Lys Phe Ala Arg
            645                 650                 655

Glu Arg Met Glu Pro Ala Ile Asp Arg Gly Phe Arg Glu Met Cys Glu
        660                 665                 670

Tyr Met Asn Asn Lys Gln His Leu Met Phe Met Asp Arg Glu Ala Ile
    675                 680                 685

Ala Gly Pro Pro Leu Gly Ser Lys Gly Ile Gly Phe Trp Thr Gly
690                 695                 700

Lys Lys Arg Tyr Ala Leu Asn Val Trp Asp Met Glu Gly Thr Arg Tyr
705                 710                 715                 720

Ala Glu Pro Lys Leu Lys Ile Met Gly Leu Glu Thr Gln Lys Ser Ser
                725                 730                 735

Thr Pro Lys Ala Val Gln Lys Ala Leu Lys Glu Cys Ile Arg Arg Met
            740                 745                 750

Leu Gln Glu Gly Glu Glu Ser Leu Gln Glu Tyr Phe Lys Glu Phe Glu
        755                 760                 765

Lys Glu Phe Arg Gln Leu Asn Tyr Ile Ser Ile Ala Ser Val Ser Ser
770                 775                 780

Ala Asn Asn Ile Ala Lys Tyr Asp Val Gly Gly Phe Pro Gly Pro Lys
785                 790                 795                 800

Cys Pro Phe His Ile Arg Gly Ile Leu Thr Tyr Asn Arg Ala Ile Lys
                805                 810                 815

Gly Asn Ile Asp Ala Pro Gln Val Val Gly Glu Lys Val Tyr Val
            820                 825                 830

Leu Pro Leu Arg Glu Gly Asn Pro Phe Gly Asp Lys Cys Ile Ala Trp
        835                 840                 845

Pro Ser Gly Thr Glu Ile Thr Asp Leu Ile Lys Asp Val Leu His
    850                 855                 860

Trp Met Asp Tyr Thr Val Leu Leu Glu Lys Thr Phe Ile Lys Pro Leu
865                 870                 875                 880

Glu Gly Phe Thr Ser Ala Ala Lys Leu Asp Tyr Glu Lys Lys Ala Ser
                885                 890                 895

Leu Phe Asp Met Phe Asp Phe
            900

<210> SEQ ID NO 2
<211> LENGTH: 14
<212> TYPE: DNA
<213> ORGANISM: Artificial Sequence
<220> FEATURE:
<223> OTHER INFORMATION: Synthetic DNA primer

<400> SEQUENCE: 2
gcggactgct tacc                                                14

<210> SEQ ID NO 3
<211> LENGTH: 18
<212> TYPE: DNA
<213> ORGANISM: Artificial Sequence
<220> FEATURE:
<223> OTHER INFORMATION: Synthetic DNA template

<400> SEQUENCE: 3
acaggtaagc agtccgcg                                            18
```

<210> SEQ ID NO 4
<211> LENGTH: 575
<212> TYPE: PRT
<213> ORGANISM: Bacillus phage phi29

<400> SEQUENCE: 4

```
Met Lys His Met Pro Arg Lys Met Tyr Ser Cys Ala Phe Glu Thr Thr
 1               5                  10                  15

Thr Lys Val Glu Asp Cys Arg Val Trp Ala Tyr Gly Tyr Met Asn Ile
            20                  25                  30

Glu Asp His Ser Glu Tyr Lys Ile Gly Asn Ser Leu Asp Glu Phe Met
        35                  40                  45

Ala Trp Val Leu Lys Val Gln Ala Asp Leu Tyr Phe His Asn Leu Lys
50                  55                  60

Phe Ala Gly Ala Phe Ile Ile Asn Trp Leu Glu Arg Asn Gly Phe Lys
65                  70                  75                  80

Trp Ser Ala Asp Gly Leu Pro Asn Thr Tyr Asn Thr Ile Ile Ser Arg
                85                  90                  95

Met Gly Gln Trp Tyr Met Ile Asp Ile Cys Leu Gly Tyr Lys Gly Lys
            100                 105                 110

Arg Lys Ile His Thr Val Ile Tyr Asp Ser Leu Lys Lys Leu Pro Phe
        115                 120                 125

Pro Val Lys Lys Ile Ala Lys Asp Phe Lys Leu Thr Val Leu Lys Gly
130                 135                 140

Asp Ile Asp Tyr His Lys Glu Arg Pro Val Gly Tyr Lys Ile Thr Pro
145                 150                 155                 160

Glu Glu Tyr Ala Tyr Ile Lys Asn Asp Ile Gln Ile Ala Glu Ala
                165                 170                 175

Leu Leu Ile Gln Phe Lys Gln Gly Leu Asp Arg Met Thr Ala Gly Ser
            180                 185                 190

Asp Ser Leu Lys Gly Phe Lys Asp Ile Ile Thr Thr Lys Lys Phe Lys
        195                 200                 205

Lys Val Phe Pro Thr Leu Ser Leu Gly Leu Asp Lys Glu Val Arg Tyr
210                 215                 220

Ala Tyr Arg Gly Gly Phe Thr Trp Leu Asn Asp Arg Phe Lys Glu Lys
225                 230                 235                 240

Glu Ile Gly Glu Gly Met Val Phe Asp Val Asn Ser Leu Tyr Pro Ala
                245                 250                 255

Gln Met Tyr Ser Arg Leu Leu Pro Tyr Gly Glu Pro Ile Val Phe Glu
            260                 265                 270

Gly Lys Tyr Val Trp Asp Glu Asp Tyr Pro Leu His Ile Gln His Ile
        275                 280                 285

Arg Cys Glu Phe Glu Leu Lys Glu Gly Tyr Ile Pro Thr Ile Gln Ile
290                 295                 300

Lys Arg Ser Arg Phe Tyr Lys Gly Asn Glu Tyr Leu Lys Ser Ser Gly
305                 310                 315                 320

Gly Glu Ile Ala Asp Leu Trp Leu Ser Asn Val Asp Leu Glu Leu Met
                325                 330                 335

Lys Glu His Tyr Asp Leu Tyr Asn Val Glu Tyr Ile Ser Gly Leu Lys
            340                 345                 350

Phe Lys Ala Thr Thr Gly Leu Phe Lys Asp Phe Ile Asp Lys Trp Thr
        355                 360                 365

Tyr Ile Lys Thr Thr Ser Glu Gly Ala Ile Lys Gln Leu Ala Lys Leu
370                 375                 380
```

```
Met Leu Asn Ser Leu Tyr Gly Lys Phe Ala Ser Asn Pro Asp Val Thr
385                 390                 395                 400
Gly Lys Val Pro Tyr Leu Lys Glu Asn Gly Ala Leu Gly Phe Arg Leu
                405                 410                 415
Gly Glu Glu Glu Thr Lys Asp Pro Val Tyr Thr Pro Met Gly Val Phe
            420                 425                 430
Ile Thr Ala Trp Ala Arg Tyr Thr Thr Ile Thr Ala Ala Gln Ala Cys
        435                 440                 445
Tyr Asp Arg Ile Ile Tyr Cys Asp Thr Asp Ser Ile His Leu Thr Gly
    450                 455                 460
Thr Glu Ile Pro Asp Val Ile Lys Asp Ile Val Asp Pro Lys Lys Leu
465                 470                 475                 480
Gly Tyr Trp Ala His Glu Ser Thr Phe Lys Arg Ala Lys Tyr Leu Arg
                485                 490                 495
Gln Lys Thr Tyr Ile Gln Asp Ile Tyr Met Lys Glu Val Asp Gly Lys
            500                 505                 510
Leu Val Glu Gly Ser Pro Asp Asp Tyr Thr Asp Ile Lys Phe Ser Val
        515                 520                 525
Lys Cys Ala Gly Met Thr Asp Lys Ile Lys Lys Glu Val Thr Phe Glu
    530                 535                 540
Asn Phe Lys Val Gly Phe Ser Arg Lys Met Lys Pro Lys Pro Val Gln
545                 550                 555                 560
Val Pro Gly Gly Val Val Leu Val Asp Asp Thr Phe Thr Ile Lys
                565                 570                 575

<210> SEQ ID NO 5
<211> LENGTH: 10
<212> TYPE: DNA
<213> ORGANISM: Artificial Sequence
<220> FEATURE:
<223> OTHER INFORMATION: Synthetic DNA primer

<400> SEQUENCE: 5
gactgcttac                                                                10

<210> SEQ ID NO 6
<211> LENGTH: 17
<212> TYPE: DNA
<213> ORGANISM: Artificial Sequence
<220> FEATURE:
<223> OTHER INFORMATION: Synthetic DNA template

<400> SEQUENCE: 6
ctaacacgta agcagtc                                                        17
```